(12) United States Patent
Gelbart

(10) Patent No.: US 8,615,856 B1
(45) Date of Patent: Dec. 31, 2013

(54) APPARATUS AND METHOD FOR FORMING SELF-RETAINING SUTURES

(75) Inventor: Daniel Gelbart, Vancouver (CA)

(73) Assignee: Ethicon, Inc., Somerville, NJ (US)

( * ) Notice: Subject to any disclaimer, the term of this patent is extended or adjusted under 35 U.S.C. 154(b) by 1146 days.

(21) Appl. No.: 12/363,582

(22) Filed: Jan. 30, 2009

Related U.S. Application Data

(60) Provisional application No. 61/006,773, filed on Jan. 30, 2008.

(51) Int. Cl.
*B21F 25/00* (2006.01)
*A61B 17/04* (2006.01)

(52) U.S. Cl.
USPC .............................................. 29/7.1; 606/146

(58) Field of Classification Search
USPC ............... 29/7.1, 7.2, 7.3; 606/146, 228, 215, 606/224, 216; 83/651
See application file for complete search history.

(56) References Cited

U.S. PATENT DOCUMENTS

| | | | |
|---|---|---|---|
| 709,392 A | 9/1902 | Brown | |
| 733,723 A | 7/1903 | Lukens | |
| 816,026 A | 3/1906 | Meier | |
| 1,142,510 A | 6/1915 | Engle | |
| 1,728,316 A | 9/1929 | Von Wachenfeldt | |
| 1,886,721 A | 11/1932 | O'Brien | |
| 2,094,578 A | 10/1937 | Blumenthal et al. | |
| 2,201,610 A | 5/1940 | Dawson, Jr. | |
| 2,232,142 A | 2/1941 | Schumann | |
| 2,254,620 A | 9/1941 | Miller | |
| 2,347,956 A | 5/1944 | Lansing | |
| 2,355,907 A | 8/1944 | Cox | |
| 2,421,193 A | 5/1947 | Gardner | |
| 2,452,734 A | 11/1948 | Costelow | |
| 2,472,009 A | 5/1949 | Gardner | |
| 2,480,271 A | 8/1949 | Sumner | |
| 2,572,936 A | 10/1951 | Kulp et al. | |
| 2,684,070 A | 7/1954 | Kelsey | |

(Continued)

FOREIGN PATENT DOCUMENTS

| | | |
|---|---|---|
| BE | 1014364 | 9/2003 |
| CA | 2309844 | 12/1996 |

(Continued)

OTHER PUBLICATIONS

Bacci, Pier Antonio, "Chirurgia Estetica Mini Invasiva Con Fili Di Sostegno", Collana di Arti, Pensiero e Scienza; Minelli Editore—2006; 54 pgs.

(Continued)

*Primary Examiner* — John C Hong

(57) ABSTRACT

An apparatus and method for forming retainers on a continuous strand such as, for example, of suture material and a suture produced by the same. The apparatus may include a retainer forming member configured to rotate about a first axis. The retainer forming member may include a cutter, the cutting edge of which may directed substantially inward toward, or outward away from, the first axis to define a retainer forming zone when the retainer forming member rotates about the first axis. The apparatus may further include a support member arranged adjacent to the retainer forming member and configured to receive and support the continuous strand in the retainer forming zone. When the retainer forming member rotates about the first axis, the passing strand may be intermittently or continuously cut by the cutting edge of the cutter.

5 Claims, 12 Drawing Sheets

(56) References Cited

U.S. PATENT DOCUMENTS

| | | |
|---|---|---|
| 2,736,964 A | 3/1956 | Lieberman |
| 2,779,083 A | 1/1957 | Enton |
| 2,817,339 A | 12/1957 | Sullivan |
| 2,866,256 A | 12/1958 | Matlin |
| 2,910,067 A | 10/1959 | White |
| 2,928,395 A | 3/1960 | Forbes et al. |
| 2,988,028 A | 6/1961 | Alcamo |
| 3,003,155 A | 10/1961 | Mielzynski et al. |
| 3,066,452 A | 12/1962 | Bott et al. |
| 3,066,673 A | 12/1962 | Bott et al. |
| 3,068,869 A | 12/1962 | Shelden et al. |
| 3,068,870 A | 12/1962 | Levin |
| 3,123,077 A | 3/1964 | Alcamo |
| 3,166,072 A | 1/1965 | Sullivan, Jr. |
| 3,187,752 A | 6/1965 | Glick |
| 3,206,018 A | 9/1965 | Lewis et al. |
| 3,209,652 A | 10/1965 | Burgsmueller |
| 3,209,754 A | 10/1965 | Brown |
| 3,212,187 A | 10/1965 | Benedict |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling |
| 3,385,299 A | 5/1968 | LeRoy |
| 3,494,006 A | 2/1970 | Brumlik |
| 3,522,637 A | 8/1970 | Brumlik |
| 3,525,340 A | 8/1970 | Gilbert |
| 3,545,608 A | 12/1970 | Berger et al. |
| 3,557,795 A | 1/1971 | Hirsch |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,618,447 A | 11/1971 | Goins |
| 3,646,615 A | 3/1972 | Ness |
| 3,683,926 A | 8/1972 | Suzuki |
| 3,716,058 A | 2/1973 | Tanner, Jr. |
| 3,720,055 A | 3/1973 | de Mestral et al. |
| 3,748,701 A | 7/1973 | De Mestral |
| 3,762,418 A | 10/1973 | Wasson |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,889,322 A | 6/1975 | Brumlik |
| 3,918,455 A | 11/1975 | Coplan |
| 3,941,164 A | 3/1976 | Musgrave |
| 3,951,261 A | 4/1976 | Mandel et al. |
| 3,977,937 A | 8/1976 | Candor |
| 3,980,177 A | 9/1976 | McGregor |
| 3,981,051 A | 9/1976 | Brumlik |
| 3,981,307 A | 9/1976 | Borysko |
| 3,985,138 A | 10/1976 | Jarvik |
| 3,985,227 A | 10/1976 | Thyen et al. |
| 3,990,144 A | 11/1976 | Schwartz |
| 4,006,747 A | 2/1977 | Kronenthal et al. |
| 4,008,303 A | 2/1977 | Glick et al. |
| 4,027,608 A | 6/1977 | Arbuckle |
| 4,043,344 A | 8/1977 | Landi et al. |
| D246,911 S | 1/1978 | Bess, Jr. et al. |
| 4,069,825 A | 1/1978 | Akiyama |
| 4,073,298 A | 2/1978 | Le Roy |
| 4,137,921 A | 2/1979 | Okuzumi et al. |
| 4,182,340 A | 1/1980 | Spencer |
| 4,186,239 A | 1/1980 | Mize et al. |
| 4,198,734 A | 4/1980 | Brumlik |
| 4,204,541 A | 5/1980 | Kapitanov |
| 4,204,542 A | 5/1980 | Bokros et al. |
| 4,259,959 A | 4/1981 | Walker |
| 4,278,374 A * | 7/1981 | Wolosianski .................. 409/74 |
| 4,300,424 A | 11/1981 | Flinn et al. |
| 4,311,002 A | 1/1982 | Hoffmann et al. |
| 4,313,448 A | 2/1982 | Stokes |
| 4,316,469 A | 2/1982 | Kapitanov |
| 4,317,451 A | 3/1982 | Cerwin et al. |
| 4,372,293 A | 2/1983 | Vijil-Rosales |
| 4,428,376 A | 1/1984 | Mericle |
| 4,430,998 A | 2/1984 | Harvey et al. |
| 4,434,796 A | 3/1984 | Karapetian |
| 4,449,298 A | 5/1984 | Putz |
| 4,454,875 A | 6/1984 | Pratt et al. |
| 4,467,805 A | 8/1984 | Fukuda |
| 4,490,326 A | 12/1984 | Beroff et al. |
| 4,492,075 A | 1/1985 | Faure |
| 4,493,323 A | 1/1985 | Albright et al. |
| 4,505,274 A | 3/1985 | Speelman |
| 4,510,934 A | 4/1985 | Batra |
| 4,531,522 A | 7/1985 | Bedi et al. |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto et al. |
| 4,610,250 A | 9/1986 | Green |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,689,882 A | 9/1987 | Lorenz |
| 4,702,250 A | 10/1987 | Ovil et al. |
| 4,719,917 A | 1/1988 | Barrows et al. |
| 4,741,330 A | 5/1988 | Hayhurst |
| 4,750,910 A | 6/1988 | Takayanagi et al. |
| 4,776,337 A | 10/1988 | Palmaz |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays et al. |
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuk et al. |
| 4,930,945 A | 6/1990 | Arai et al. |
| 4,932,962 A | 6/1990 | Yoon et al. |
| 4,946,468 A | 8/1990 | Li |
| 4,948,444 A | 8/1990 | Schutz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini |
| 4,981,149 A | 1/1991 | Yoon |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,101,968 A | 4/1992 | Henderson et al. |
| 5,102,418 A | 4/1992 | Granger et al. |
| 5,102,421 A | 4/1992 | Anspach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |

(56) References Cited

U.S. PATENT DOCUMENTS

| | | |
|---|---|---|
| 5,147,382 A | 9/1992 | Gertzman et al. |
| 5,156,615 A | 10/1992 | Korthoff et al. |
| 5,156,788 A | 10/1992 | Chesterfield et al. |
| 5,176,692 A | 1/1993 | Wilk et al. |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,234,006 A | 8/1993 | Eaton et al. |
| 5,242,457 A | 9/1993 | Akopov et al. |
| 5,246,441 A | 9/1993 | Ross et al. |
| 5,249,673 A | 10/1993 | Sinn |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green |
| 5,306,288 A | 4/1994 | Granger et al. |
| 5,306,290 A | 4/1994 | Martins et al. |
| 5,320,629 A | 6/1994 | Noda et al. |
| 5,330,488 A | 7/1994 | Goldrath |
| 5,330,503 A | 7/1994 | Yoon |
| 5,341,922 A | 8/1994 | Cerwin et al. |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,391,173 A | 2/1995 | Wilk |
| 5,403,346 A | 4/1995 | Loeser |
| 5,411,523 A | 5/1995 | Goble |
| 5,414,988 A | 5/1995 | DiPalma et al. |
| 5,417,691 A | 5/1995 | Hayhurst |
| 5,425,746 A | 6/1995 | Proto et al. |
| 5,425,747 A | 6/1995 | Brotz |
| 5,437,680 A | 8/1995 | Yoon |
| 5,450,860 A | 9/1995 | O'Connor |
| 5,451,461 A | 9/1995 | Broyer |
| 5,462,561 A | 10/1995 | Voda |
| 5,464,426 A | 11/1995 | Bonutti |
| 5,464,427 A | 11/1995 | Curtis et al. |
| 5,472,452 A | 12/1995 | Trott |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A | 1/1996 | Le et al. |
| 5,494,154 A | 2/1996 | Ainsworth et al. |
| 5,500,000 A | 3/1996 | Feagin et al. |
| 5,500,991 A | 3/1996 | Demarest et al. |
| 5,520,084 A | 5/1996 | Chesterfield et al. |
| 5,520,691 A | 5/1996 | Branch |
| 5,522,845 A | 6/1996 | Wenstrom, Jr. |
| 5,527,342 A | 6/1996 | Pietrzak et al. |
| 5,531,760 A | 7/1996 | Alwafaie |
| 5,531,761 A | 7/1996 | Yoon |
| 5,531,790 A | 7/1996 | Frechet et al. |
| 5,536,582 A | 7/1996 | Prasad et al. |
| 5,540,705 A | 7/1996 | Meade et al. |
| 5,540,718 A | 7/1996 | Bartlett |
| 5,545,148 A | 8/1996 | Wurster |
| 5,549,631 A | 8/1996 | Bonutti |
| 5,554,171 A | 9/1996 | Gatturna et al. |
| 5,566,822 A | 10/1996 | Scanlon |
| 5,569,272 A | 10/1996 | Reed et al. |
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,601,557 A | 2/1997 | Hayhurst |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo et al. |
| 5,662,714 A | 9/1997 | Charvin et al. |
| 5,669,935 A | 9/1997 | Rosenman et al. |
| 5,676,675 A | 10/1997 | Grice |
| 5,683,417 A | 11/1997 | Cooper |
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |
| 5,716,358 A | 2/1998 | Ochoa et al. |
| 5,716,376 A | 2/1998 | Roby et al. |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans et al. |
| 5,731,855 A | 3/1998 | Koyama et al. |
| 5,741,277 A | 4/1998 | Gordon et al. |
| 5,744,151 A | 4/1998 | Capelli |
| 5,763,411 A | 6/1998 | Edwardson et al. |
| 5,765,560 A | 6/1998 | Verkerke et al. |
| 5,766,246 A | 6/1998 | Mulhauser et al. |
| 5,779,719 A | 7/1998 | Klein et al. |
| 5,782,864 A | 7/1998 | Lizardi |
| 5,807,403 A | 9/1998 | Beyar et al. |
| 5,807,406 A | 9/1998 | Brauker et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,855,619 A | 1/1999 | Caplan et al. |
| 5,863,360 A | 1/1999 | Wood et al. |
| 5,887,594 A | 3/1999 | LoCicero, III |
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,899,911 A | 5/1999 | Carter |
| 5,916,224 A | 6/1999 | Esplin |
| 5,919,234 A | 7/1999 | Lemperle et al. |
| 5,925,078 A | 7/1999 | Anderson |
| 5,931,855 A | 8/1999 | Buncke |
| 5,938,668 A | 8/1999 | Scirica et al. |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 6,001,111 A | 12/1999 | Sepetka et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,039,741 A | 3/2000 | Meislin |
| 6,056,778 A | 5/2000 | Grafton et al. |
| 6,063,105 A | 5/2000 | Totakura |

(56) References Cited

U.S. PATENT DOCUMENTS

| | | |
|---|---|---|
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,146,406 A | 11/2000 | Shluzas et al. |
| 6,146,407 A | 11/2000 | Krebs |
| 6,149,660 A | 11/2000 | Laufer et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,203,565 B1 | 3/2001 | Bonutti et al. |
| 6,206,908 B1 | 3/2001 | Roby |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,463,719 B2 | 10/2002 | Dey et al. |
| 6,471,715 B1 | 10/2002 | Weiss |
| 6,478,809 B1 | 11/2002 | Brotz |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,511,488 B1 | 1/2003 | Marshall et al. |
| 6,514,265 B2 | 2/2003 | Ho et al. |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,648,921 B2 | 11/2003 | Anderson et al. |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,859 B2 | 3/2004 | Rousseau et al. |
| 6,716,234 B2 | 4/2004 | Grafton et al. |
| 6,720,402 B2 | 4/2004 | Langer et al. |
| 6,726,705 B2 | 4/2004 | Peterson et al. |
| 6,746,443 B1 | 6/2004 | Morley et al. |
| 6,746,458 B1 | 6/2004 | Cloud |
| 6,749,616 B1 | 6/2004 | Nath |
| 6,773,450 B2 | 8/2004 | Leung et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |
| 6,852,825 B2 | 2/2005 | Lendlein et al. |
| 6,858,222 B2 | 2/2005 | Nelson et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,945,021 B2 | 9/2005 | Michel |
| 6,945,980 B2 | 9/2005 | Nguyen et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,033,603 B2 | 4/2006 | Nelson et al. |
| 7,037,984 B2 | 5/2006 | Lendlein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |
| 7,070,610 B2 | 7/2006 | Im et al. |
| 7,081,135 B2 | 7/2006 | Smith et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | Del Rio et al. |
| 7,150,757 B2 | 12/2006 | Fallin et al. |
| 7,156,858 B2 | 1/2007 | Schuldt-Hempe et al. |
| 7,156,862 B2 | 1/2007 | Jacobs et al. |
| 7,160,312 B2 | 1/2007 | Saadat |
| 7,166,570 B2 | 1/2007 | Hunter et al. |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et al. |
| 7,214,230 B2 | 5/2007 | Brock et al. |
| 7,217,744 B2 | 5/2007 | Lendlein et al. |
| 7,225,512 B2 * | 6/2007 | Genova et al. .................. 29/7.1 |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,297,142 B2 | 11/2007 | Brock |
| 7,322,105 B2 | 1/2008 | Lewis |
| 7,371,253 B2 | 5/2008 | Leung et al. |
| 7,513,904 B2 | 4/2009 | Sulamanidze et al. |
| 7,514,095 B2 | 4/2009 | Nelson et al. |

(56) References Cited

U.S. PATENT DOCUMENTS

| | | |
|---|---|---|
| 7,582,105 B2 | 9/2009 | Kolster |
| 7,601,164 B2 | 10/2009 | Wu |
| 7,624,487 B2 | 12/2009 | Trull et al. |
| 7,645,293 B2 | 1/2010 | Martinek et al. |
| 7,806,908 B2 | 10/2010 | Ruff |
| 7,879,072 B2 | 2/2011 | Bonutti et al. |
| 7,919,112 B2 | 4/2011 | Pathak et al. |
| 8,118,834 B1 | 2/2012 | Goraltchouk et al. |
| 8,216,273 B1 | 7/2012 | Goraltchouk et al. |
| 8,226,684 B2 | 7/2012 | Nawrocki et al. |
| 8,308,761 B2 | 11/2012 | Brailovski et al. |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0039450 A1 | 11/2001 | Pavcnik et al. |
| 2001/0051807 A1 | 12/2001 | Grafton |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0077448 A1 | 6/2002 | Antal et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0173822 A1 | 11/2002 | Justin et al. |
| 2003/0040795 A1 | 2/2003 | Elson et al. |
| 2003/0069602 A1 | 4/2003 | Jacobs et al. |
| 2003/0088270 A1 | 5/2003 | Lubbers et al. |
| 2003/0149447 A1 | 8/2003 | Morency |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1 | 10/2003 | Keane et al. |
| 2003/0225424 A1 | 12/2003 | Benderev |
| 2003/0229361 A1 | 12/2003 | Jackson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0030354 A1 | 2/2004 | Leung et al. |
| 2004/0039415 A1 | 2/2004 | Zamierowski |
| 2004/0049224 A1 | 3/2004 | Buehlmann et al. |
| 2004/0059370 A1 | 3/2004 | Greene, Jr. et al. |
| 2004/0059377 A1 | 3/2004 | Peterson et al. |
| 2004/0060409 A1 | 4/2004 | Leung et al. |
| 2004/0060410 A1 | 4/2004 | Leung et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0167575 A1 | 8/2004 | Roby |
| 2004/0186487 A1 | 9/2004 | Klein et al. |
| 2004/0193191 A1 | 9/2004 | Starksen et al. |
| 2004/0193217 A1 | 9/2004 | Lubbers et al. |
| 2004/0193257 A1 | 9/2004 | Wu et al. |
| 2004/0226427 A1* | 11/2004 | Trull et al. ............ 83/651 |
| 2004/0230223 A1 | 11/2004 | Bonutti et al. |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0034431 A1 | 2/2005 | Dey et al. |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko et al. |
| 2005/0065533 A1 | 3/2005 | Magen et al. |
| 2005/0070959 A1 | 3/2005 | Cichocki et al. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0113936 A1 | 5/2005 | Brustad et al. |
| 2005/0119694 A1 | 6/2005 | Jacobs et al. |
| 2005/0125020 A1 | 6/2005 | Meade et al. |
| 2005/0125034 A1 | 6/2005 | Cichocki et al. |
| 2005/0125035 A1 | 6/2005 | Cichocki et al. |
| 2005/0149064 A1 | 7/2005 | Peterson et al. |
| 2005/0149118 A1 | 7/2005 | Koyfman et al. |
| 2005/0154255 A1 | 7/2005 | Jacobs |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182445 A1 | 8/2005 | Zamierowski |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamanidze et al. |
| 2005/0209542 A1 | 9/2005 | Jacobs et al. |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0267531 A1 | 12/2005 | Ruff et al. |
| 2005/0267532 A1 | 12/2005 | Wu |
| 2005/0277984 A1 | 12/2005 | Long |
| 2005/0283246 A1 | 12/2005 | Cauthen, III et al. |
| 2006/0020272 A1 | 1/2006 | Gildenberg |
| 2006/0030884 A1 | 2/2006 | Young et al. |
| 2006/0036266 A1 | 2/2006 | Sulamanidze et al. |
| 2006/0058470 A1 | 3/2006 | Rizk |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079469 A1 | 4/2006 | Anderson et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0111734 A1 | 5/2006 | Kaplan et al. |
| 2006/0111742 A1 | 5/2006 | Kaplan et al. |
| 2006/0122608 A1 | 6/2006 | Fallin et al. |
| 2006/0135994 A1 | 6/2006 | Ruff |
| 2006/0135995 A1 | 6/2006 | Ruff |
| 2006/0142784 A1 | 6/2006 | Kontos |
| 2006/0193769 A1 | 8/2006 | Nelson et al. |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235445 A1 | 10/2006 | Birk et al. |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin et al. |
| 2006/0253126 A1 | 11/2006 | Bjerken et al. |
| 2006/0257629 A1 | 11/2006 | Lendlein et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0282099 A1 | 12/2006 | Stokes et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2006/0293710 A1 | 12/2006 | Foerster et al. |
| 2007/0005109 A1 | 1/2007 | Popadiuk et al. |
| 2007/0005110 A1 | 1/2007 | Collier et al. |

(56) References Cited

U.S. PATENT DOCUMENTS

| | | |
|---|---|---|
| 2007/0021779 A1 | 1/2007 | Garvin et al. |
| 2007/0027475 A1 | 2/2007 | Pagedas |
| 2007/0038249 A1 | 2/2007 | Kolster |
| 2007/0065663 A1 | 3/2007 | Trull et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0135843 A1 | 6/2007 | Burkhart |
| 2007/0151961 A1 | 7/2007 | Kleine et al. |
| 2007/0156175 A1 | 7/2007 | Weadock et al. |
| 2007/0167958 A1 | 7/2007 | Sulamanidze et al. |
| 2007/0187861 A1 | 8/2007 | Genova et al. |
| 2007/0208355 A1 | 9/2007 | Ruff |
| 2007/0208377 A1 | 9/2007 | Kaplan et al. |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0225763 A1 | 9/2007 | Zwolinski et al. |
| 2007/0227914 A1 | 10/2007 | Cerwin et al. |
| 2007/0233188 A1 | 10/2007 | Hunt et al. |
| 2007/0239206 A1 | 10/2007 | Shelton, IV et al. |
| 2007/0239207 A1 | 10/2007 | Beramendi |
| 2007/0257395 A1 | 11/2007 | Lindh et al. |
| 2007/0282247 A1 | 12/2007 | Desai et al. |
| 2007/0293892 A1 | 12/2007 | Takasu |
| 2008/0004490 A1 | 1/2008 | Bosley, Jr. et al. |
| 2008/0004603 A1 | 1/2008 | Larkin et al. |
| 2008/0009838 A1 | 1/2008 | Schena et al. |
| 2008/0009888 A1 | 1/2008 | Ewers et al. |
| 2008/0009902 A1 | 1/2008 | Hunter et al. |
| 2008/0027273 A1 | 1/2008 | Gutterman |
| 2008/0027486 A1 | 1/2008 | Jones et al. |
| 2008/0046094 A1 | 2/2008 | Han et al. |
| 2008/0058869 A1 | 3/2008 | Stopek et al. |
| 2008/0064839 A1 | 3/2008 | Hadba et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0109036 A1 | 5/2008 | Stopek et al. |
| 2008/0131692 A1 | 6/2008 | Rolland et al. |
| 2008/0132943 A1 | 6/2008 | Maiorino et al. |
| 2008/0169059 A1 | 7/2008 | Messersmith et al. |
| 2008/0195147 A1 | 8/2008 | Stopek |
| 2008/0195417 A1 | 8/2008 | Surpin et al. |
| 2008/0208358 A1 | 8/2008 | Bellamkonda et al. |
| 2008/0215072 A1 | 9/2008 | Kelly |
| 2008/0221618 A1 | 9/2008 | Chen et al. |
| 2008/0234731 A1 | 9/2008 | Leung et al. |
| 2008/0248216 A1 | 10/2008 | Yeung et al. |
| 2008/0255611 A1 | 10/2008 | Hunter |
| 2008/0262542 A1 | 10/2008 | Sulamanidze et al. |
| 2008/0281338 A1 | 11/2008 | Wohlert et al. |
| 2008/0281357 A1 | 11/2008 | Sung et al. |
| 2008/0312688 A1 | 12/2008 | Nawrocki et al. |
| 2009/0012560 A1 | 1/2009 | Hunter et al. |
| 2009/0018577 A1 | 1/2009 | Leung et al. |
| 2009/0043336 A1 | 2/2009 | Yuan et al. |
| 2009/0076543 A1 | 3/2009 | Maiorino et al. |
| 2009/0082856 A1 | 3/2009 | Flanagan |
| 2009/0088835 A1 | 4/2009 | Wang |
| 2009/0099597 A1 | 4/2009 | Isse |
| 2009/0105753 A1 | 4/2009 | Greenhalgh et al. |
| 2009/0107965 A1 | 4/2009 | D'Agostino |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0200487 A1 | 8/2009 | Maiorino et al. |
| 2009/0210006 A1 | 8/2009 | Cohen et al. |
| 2009/0216253 A1 | 8/2009 | Bell et al. |
| 2009/0226500 A1 | 9/2009 | Avelar et al. |
| 2009/0248066 A1 | 10/2009 | Wilkie |
| 2009/0248067 A1 | 10/2009 | Maiorino |
| 2009/0248070 A1 | 10/2009 | Kosa et al. |
| 2009/0250356 A1 | 10/2009 | Kirsch et al. |
| 2009/0250588 A1 | 10/2009 | Robeson et al. |
| 2009/0259233 A1 | 10/2009 | Bogart et al. |
| 2009/0259251 A1 | 10/2009 | Cohen |
| 2009/0287245 A1 | 11/2009 | Ostrovsky et al. |
| 2009/0299407 A1 | 12/2009 | Yuan et al. |
| 2009/0299408 A1 | 12/2009 | Schuldt-Hempe et al. |
| 2009/0306710 A1 | 12/2009 | Lindh et al. |
| 2010/0021516 A1 | 1/2010 | McKay |
| 2010/0023055 A1 | 1/2010 | Rousseau |
| 2010/0057123 A1 | 3/2010 | D'Agostino et al. |
| 2010/0063540 A1 | 3/2010 | Maiorino |
| 2010/0071833 A1 | 3/2010 | Maiorino |
| 2010/0087855 A1 | 4/2010 | Leung et al. |
| 2010/0101707 A1 | 4/2010 | Maiorino et al. |
| 2010/0140115 A1 | 6/2010 | Kirsch |
| 2010/0160961 A1 | 6/2010 | Nawrocki et al. |
| 2010/0163056 A1 | 7/2010 | Tschopp et al. |
| 2010/0211097 A1 | 8/2010 | Hadba et al. |
| 2010/0211098 A1 | 8/2010 | Hadba et al. |
| 2010/0239635 A1 | 9/2010 | McClain et al. |
| 2010/0292718 A1 | 11/2010 | Sholev et al. |
| 2010/0294103 A1 | 11/2010 | Genova et al. |
| 2010/0294104 A1 | 11/2010 | Genova et al. |
| 2010/0294105 A1 | 11/2010 | Genova et al. |
| 2010/0294106 A1 | 11/2010 | Genova et al. |
| 2010/0294107 A1 | 11/2010 | Genova et al. |
| 2010/0298637 A1 | 11/2010 | Ruff |
| 2010/0298867 A1 | 11/2010 | Ruff |
| 2010/0298868 A1 | 11/2010 | Ruff |
| 2010/0298871 A1 | 11/2010 | Ruff et al. |
| 2010/0298878 A1 | 11/2010 | Leung et al. |
| 2010/0298879 A1 | 11/2010 | Leung et al. |
| 2010/0298880 A1 | 11/2010 | Leung et al. |
| 2010/0313723 A1 | 12/2010 | Genova et al. |
| 2010/0313729 A1 | 12/2010 | Genova et al. |
| 2010/0313730 A1 | 12/2010 | Genova et al. |
| 2010/0318122 A1 | 12/2010 | Leung et al. |
| 2010/0318123 A1 | 12/2010 | Leung et al. |
| 2011/0009902 A1 | 1/2011 | Leung et al. |
| 2011/0106152 A1* | 5/2011 | Kozlowski .................. 606/228 |

FOREIGN PATENT DOCUMENTS

| | | |
|---|---|---|
| CA | 2457384 | 3/2003 |
| CN | 2640420 | 9/2004 |
| DE | 01810800 | 6/1970 |
| DE | 03227984 | 2/1984 |
| DE | 04302895 | 8/1994 |
| DE | 19618891 | 4/1997 |
| DE | 19833703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0513713 | 5/1992 |
| EP | 0428253 | 7/1994 |
| EP | 0632999 | 1/1995 |
| EP | 0513736 | 2/1995 |
| EP | 0464479 | 3/1995 |
| EP | 0464480 | 3/1995 |
| EP | 0576337 A1 | 3/1997 |
| EP | 0576337 B1 | 3/1997 |
| EP | 0574707 | 8/1997 |
| EP | 0612504 | 11/1997 |
| EP | 0558993 | 4/1998 |
| EP | 0913123 | 5/1999 |
| EP | 0916310 | 5/1999 |
| EP | 0664198 | 6/1999 |
| EP | 0960600 | 12/1999 |
| EP | 0705567 | 3/2002 |
| EP | 0673624 | 8/2002 |
| EP | 0839499 | 9/2003 |
| EP | 0755656 | 12/2003 |

(56) References Cited

FOREIGN PATENT DOCUMENTS

| | | |
|---|---|---|
| EP | 1075843 | 2/2005 |
| EP | 1525851 | 4/2005 |
| EP | 1532942 | 5/2005 |
| EP | 0826337 | 12/2005 |
| EP | 0991359 | 11/2007 |
| EP | 1656890 | 12/2008 |
| EP | 2036502 | 3/2009 |
| EP | 1948261 | 11/2010 |
| EP | 1726317 | 7/2012 |
| EP | 2338421 | 11/2012 |
| FR | 2619129 | 2/1989 |
| FR | 2693108 | 1/1994 |
| FR | 9208059 | 3/1997 |
| GB | 0267007 | 3/1927 |
| GB | 1091282 | 11/1967 |
| GB | 1428560 | 7/1973 |
| GB | 1506362 | 4/1978 |
| GB | 1508627 | 4/1978 |
| JP | 51-130091 | 11/1976 |
| JP | 1506362 | 4/1978 |
| JP | 54-116419 | 9/1979 |
| JP | 63-500702 | 3/1988 |
| JP | 63-288146 | 11/1988 |
| JP | 001113091 | 5/1989 |
| JP | 3-165751 | 7/1991 |
| JP | 4-096758 | 3/1992 |
| JP | 4-226642 | 8/1992 |
| JP | 4-266749 | 9/1992 |
| JP | 9-103477 | 4/1997 |
| JP | 10-511009 | 10/1997 |
| JP | 10-503389 | 3/1998 |
| JP | 410085225 | 4/1998 |
| JP | 11-313826 | 11/1999 |
| JP | 011332828 | 12/1999 |
| JP | 2002-059235 | 2/2002 |
| JP | 2002-511308 | 4/2002 |
| JP | 2003-275217 | 9/2003 |
| JP | 2004-530524 | 10/2004 |
| JP | 2005-500119 | 1/2005 |
| JP | 2006-517112 | 7/2006 |
| KR | 10-2005-0072908 | 7/2005 |
| KR | 6013299 | 2/2006 |
| KR | 2006-59142 | 6/2006 |
| NZ | 501224 | 3/2002 |
| NZ | 531262 | 12/2005 |
| RU | 1823791 | 6/1993 |
| RU | 2139690 | 10/1999 |
| RU | 2175855 | 11/2001 |
| RU | 2241389 | 12/2004 |
| RU | 2268752 | 1/2006 |
| SU | 1745214 | 7/1992 |
| SU | 1752358 | 8/1992 |
| WO | WO 96/06565 | 3/1966 |
| WO | WO 86/00020 | 1/1986 |
| WO | WO 87/01270 | 3/1987 |
| WO | WO 88/09157 | 12/1988 |
| WO | WO 89/05618 | 6/1989 |
| WO | WO 90/09149 | 8/1990 |
| WO | WO 90/14795 | 12/1990 |
| WO | WO 92/22336 | 12/1992 |
| WO | WO 95/16399 | 6/1995 |
| WO | WO 98/52473 | 11/1998 |
| WO | WO 98/55031 | 12/1998 |
| WO | WO 99/21488 | 5/1999 |
| WO | WO 99/33401 | 7/1999 |
| WO | WO 99/59477 | 11/1999 |
| WO | WO 99/62431 | 12/1999 |
| WO | WO 00/51658 | 9/2000 |
| WO | WO 00/51685 | 9/2000 |
| WO | WO 01/06952 | 2/2001 |
| WO | WO 01/56626 | 8/2001 |
| WO | WO 03/001979 | 1/2003 |
| WO | WO 03/045255 | 6/2003 |
| WO | WO 03/077772 | 9/2003 |
| WO | WO 03/092758 | 11/2003 |
| WO | WO 03/103733 | 12/2003 |
| WO | WO 03/103972 | 12/2003 |
| WO | WO 03/105703 | 12/2003 |
| WO | WO 2004/014236 | 2/2004 |
| WO | WO 2004/030517 | 4/2004 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |
| WO | WO 2004/100801 | 11/2004 |
| WO | WO 2004/112853 | 12/2004 |
| WO | WO 2005/016176 | 2/2005 |
| WO | WO 2005/074913 | 8/2005 |
| WO | WO 2005/096955 | 10/2005 |
| WO | WO 2005/096956 | 10/2005 |
| WO | WO 2005/112787 | 12/2005 |
| WO | WO 2006/005144 | 1/2006 |
| WO | WO 2006/012128 | 2/2006 |
| WO | WO 2006/061868 | 6/2006 |
| WO | WO 2006/079469 | 8/2006 |
| WO | WO 2006/082060 | 8/2006 |
| WO | WO 2006/099703 | 9/2006 |
| WO | WO 2006/138300 | 12/2006 |
| WO | WO 2007/005291 | 1/2007 |
| WO | WO 2007/005296 | 1/2007 |
| WO | WO 2007/038837 | 4/2007 |
| WO | WO 2007/053812 | 5/2007 |
| WO | WO 2007/112024 | 10/2007 |
| WO | WO 2007/133103 | 11/2007 |
| WO | WO 2007/145614 | 12/2007 |
| WO | WO 2008/128113 | 10/2008 |
| WO | WO 2008/150773 | 12/2008 |
| WO | WO 2009/042841 | 4/2009 |
| WO | WO 2009/068252 | 6/2009 |
| WO | WO 2009/087105 | 7/2009 |
| WO | WO 2009/097556 | 8/2009 |
| WO | WO 2009/151876 | 12/2009 |
| WO | WO 2010/052007 | 5/2010 |

OTHER PUBLICATIONS

Behl, Marc et al., "Shape-Memory Polymers", Materials Today Apr. 2007; 10(4); 20-28.

Belkas, J. S. et al., "Peripheral nerve regeneration through a synthetic hydrogel nerve tube", Restorative Neurology and Neuroscience 23 (2005) 19-29.

Bellin, I. et al., "Polymeric triple-shape materials", Proceedings of the National Academy of Sciences of the United States of America Nov. 28, 2006; 2103(48):18043-18047.

Boenisch, U.W. et al 'Pull-Out strength and stiffness of meniscal repair using absorbable arrows or Ti-Cron vertical and horizontal loop sutures' American Journal of Sports Medicine, Sep.-Oct. (1999) vol. 27, Issue 5, pp. 626-631.

Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.

Buncke, Jr., H.J. et al 'The Suture Repair of One-Millimeter Vessels, microvascular surgery' (1966) Report of First Conference; Oct. 6-7 pp. 24-35.

Bunnell, S. 'Gig pull-out suture for tendons' J Bone Joint Surg. Am (1954) vol. 36A, No. 4 pp. 850-851.

CCPR Centro De Cirurgia Plastica e Reabilitacao 'Up Lifting (Aptos Threads) http://ccpr.com.br/upl-l.htm, Aug. 19, 2002 pp. 1-2.

Dahlin, Lars, "Techniques of Peripheral Nerve Repair", Scandinavian Journal of Surgery 97: 310-316, 2008.

Datillo, Jr., P.P. 'Knodess Bi-directional Barbed Absorbable Surgical Suture' Dissertation submitted to the Graduate Faculty of North Carolina State University Textile Management and Technology Nov. 2002, 75 pages.

Datillo, Jr. P.P. et al 'Medical Textiles: Application of an Absorbable Barbed Bi-Directional Surgical Suture' (2002) The Journal of Textile and Apparel Technology and Management vol. 2, Issue 2, pp. 1-5.

Datillo, Jr., P. et al 'Tissue holding performance of knodess absorbable sutures' Society for Biomaterials 29th Annual Meeting Transactions (2003) p. 101.

(56) References Cited

OTHER PUBLICATIONS

Declaration of Dr. Gregory L. Ruff, dated Aug. 19, 2005, 8 pages, with Exhibits A-E.
De Persia, Raúl et al., "Mechanics of Biomaterials: Sutures After the Surgery", Applications of Engineering Mechanics in Medicine, GED-University of Puerto Rico, Mayaguez May 2005, pg. F1-F27.
Delorenzi, C.L., "Barbed Sutures: Rationale and Technique", Aesthetic Surg. J. 2006 Mar 26(2): 223-229.
Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Gross, Alex, "Physician perspective on thread lifts", Dermatology Times Feb. 27, 2006 (2): 2 pages.
Gross, R.A. et al 'Biodegradable Polymers for the Environment' Science 297(5582) 803 (2002).
Han, H. et al 'Mating and Piercing Micromechanical Suture for Surface Bonding Applications' (1991) Proceedings of the 1991 Micro Electro Mechanical Systems (MEMS>91), An Investigation of Micro Structures, Sensors, Actuators, Machines and Robots pp. 253-258.
Immergut, Edmund H., Grulke, Eric A., Abe, Akihiro; Daniel R. 2005 John Wiley & Sons.
Ingle, N.P. et al 'Barbed Suture Anchoring Strength: Applicability to Dissimilar Polymeric Materials' College of Textiles, North Carolina State University, 7th World Biomaterials Congress 2004, 1 page.
Ingle, N.P. et al 'Mechanical Performance and Finite Element Analysis of Bidirectional Barbed Sutures' Master of Science in Textile Technology & Management at North Carolina State University Aug. 2003, 126 pages.
Ingle, Nilesh P et al., "Testing the Tissue-holding Capacity of Barbed Sutures", College of Textiles, North Carolina State University, Fiber Science, The Next Generation Oct. 17-19 2005, New Jersey Institute of Technology, Newark, NJ, 4 pages.
Jennings et al 'A New Technique in primary tendon repair' Surg. Gynecol. Obstet. (1952) vol. 95, No. 5 pp. 597-600.
Jeong, H.E. et al 'A nontransferring dry adhesive with hierarchial polymer nanohairs' PNAS 106 (14) pp. 5639-5644 (2009).
Kaminer, M. et al., "ContourLift™: A New Method of Minimally Invasive Facial Rejuvenation", Cosmetic Dermatology Jan. 2000; 20(1): 29-35.
Kelch et al., "Shape-memory Polymer Networks from Olio[(∈-hydroxycaproate)-co-glycolate]dimethacrylates and Butyl Acrylate with Adjustable Hydrolytic Degradation Rate", Biomacromolecules 2007;8(3):1018-1027.
Khademhosseini, Ali et al., "Nanobiotechnology Drug Delivery and Tissue Engineering", Chemical Engineering Progress 102:38-42 (2006).
Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.
Lendelin, A. et al 'Biodegradable, Elastic Shape-Memory Polymers for Potential Biomedical Applications' (2002) Science vol. 296 pp. 1673-1676.
Lendelin, A. et al 'Shape-Memory Polymers' Agnew Chem. Int. Ed. (2002) vol. 41 pp. 2034-2057.
Leung, J. et al 'Barbed, Bi-directional Medical Sutures: Biomechanical Properties and Wound Closure Efficacy Study' 2002 Society for Biomaterials 28th Annual Meeting Transactions 1 page.
Leung, J. et al 'Barbed, Bi-directional Surgical Sutures' International Conference & Exhibition on Healthcare & Medical Textiles, Jul. 8-9, 2003 pp. 1-8.
Leung, J. et al 'Barbed, Bi-directional Surgical Sutures: In Vivo Strength and Histopathology Evaluations' 2003 Society for Biomaterials 29th Annual Meeting Transactions p. 100.
Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.
Leung, J. et al 'Performance Enhancement of a Knotless Suture via Barb Geometry Modifications' 7th World Biomaterials Congress 2004, 1 page.
Li, Y.Y. et al 'Polymer Replicas of Photonic Porous Silicon for Sensing and Drug Delivery Applications' (2003) Science vol. 299 pp. 2045-2047.
Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.
Madduri, Srinivas, et al., "Neurotrophic factors release from nerve conduits for peripheral axonal regeneration", European Cells and Materials vol. 16; Suppl. 1 (2008), p. 14.
Madhave et al 'A biodegradable and biocompatible gecko-inspired tissue adhesive' PNAS 105(7) pp. 2307-2312 (2008).
Maitland et al., "Prototype laser-activated shape memory polymer foam device for embolic treatment of aneurysms", Journal of Biomedical Optics May/Jun. 2007;12(3): pp. 030504-1 to 030504-3.
Malina, M. et al 'Endovascular AAA Exclusion: Will Stents with Hooks and Barbs Prevent Stent-Graft Migration' Journal Endovascular Surgery (1998) vol. 5 pp. 310-317.
Mansberger et al 'A New Type Pull-Out Wire for Tendon Surgery: A Preliminary Report' Department of Surgery, University Hospital and University of Maryland School of Medicine, Baltimore, Maryland, Received for Publication May 10, 1951 pp. 119-121.
Martin, D.P. et al 'Medical applications of poly-4-hydroxybutyrate: a strong flexible absorbable biomaterial' Biochemical Engineering Journal vol. 16 (2003) pp. 97-105.
Mason, M.L. 'Primary and Secondary Tendon Suture. A discussion of the significance of technique in tendon surgery' (1940) Surg Gynecol Obstet 70.
McKee, GK 'Metal anastomosis tubes in tendon suture' The Lancet (1945) pp. 659-660.
McKenzie 'An Experimental Multiple Barbed Suture for the Long Flexor Tendons of the Palm and Fingers' The Journal of Bone and Joint Surgery (1967) vol. 49B, No. 3 pp. 440-447.
Middleton and Tipton 'Synthetic Biodegradable Polymers as Medical Devices' (1998) Medical Plastics and Biomaterials Magazine.
Moran et al., "Bidirectional-Barbed Sutured Knodess Running Anastomosis v Classic van Velthovan in a Model System", Journal of Endourology Oct. 2007; 21(10); 1175-1177.
Mullner, "Metal Foam Has a Good Memory", Dec. 18, 2007 Original story at <http.//www.physorg.com/news117214996.html>.
Murtha et al., "Evaluation of a Novel Technique for Wound Closure Using A Barbed Suture", Journal of the American Society of Plastic Surgeons 2006; 117(6); 1769-1780.
Nie, Zhihong and Kumacheva, Eugenia, "Patterning surfaces with functional polymers", Nature Materials vol. 7(2008): 277-290.
Paul, Malcolm D., "Bidirectional Barbed Sutures for Wound Closure: Evolution and Applications", Journal of the American College of Certified Wound Specialists (2009) 1, 51-57.
Paul, Malcolm D. and Rui Avelar, "Quill™ SRS Techniques & Procedures A Novel Approach to Soft Tissue Approximation", Canada, Angiotech Pharmaceuticals, Inc., Third Edition 2009, 8 2007-2009: 27 pages.
Paul, Malcolm D. and Rui Avelar, "Quill™ SRS Techniques & Procedures A Novel Approach to Soft Tissue Approximation", Canada, Angiotech Pharmaceuticals, Inc., Fourth Edition 2010, 8 2007-2010: 27 pages.
Paul, Malcolm D., "Using Barbed Sutures in Open/Subperiosteal Midface Lifting", Aesthetic Surgery Journal 2006(26): 725-732.
Potenza, A. 'Tendon Healing Within the Flexor Digital Sheath in the Dog: An Experimental Study' Journal of Bone & Joint Surgery (1962) vol. 44A No. 1 pp. 49-64.
Pulvertaft 'Suture Materials and Tendon Junctures' American Journal of Surgery (1965) vol. 109 pp. 346-352.
Quill Medical, Inc. 'Barbed Sutures, wrinkle filters give patients more innovative, non-surgical options' Press Release of Program presented at American Society of Plastic Surgeons annual scientific meeting; Philadelphia, Oct. 9, 2004 3 pages.

(56) References Cited

OTHER PUBLICATIONS

Quill Medical, Inc. 'Quill Medical's Novel-Self-Anchoring Surgical Suture Approved for Sale in Europe' Press Release; Research Triangle Park, N.C. May 10, 2004, 1 page.
Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page
Richert, Ludovic, et al., "Surface Nanopatterning to Control Cell Growth", Advanced Materials 2008(15): 1-5.
Rodeheaver, G.T. et al., "Barbed Sutures for Wound Closure: In Vivo Wound Security, Tissue Compatibility and Cosmesis Measurements", Society for Biomaterials 30th Annual Meeting Transactions, 2005, 2 pages.
Rofin-Baasel 'Laser Marking on Plastic Materials' (2001) RB50.0, Rofin-Baasel Inc. 2 pages.
Ruff, Gregory, "Technique and Uses for Absorbable Barbed Sutures", Aesthetic Surgery Journal Sep./Oct. 2006; 26:620-628.
Scherman, Peter et al., "Sutures as longitudinal guides for the repair of nerve defects-Influence of suture numbers and reconstruction of nerve bifurcations", Restorative Neurology and Neuroscience 23 (2005) 79-85.
Semenov, G.M. et al 'Surgical Suture' (2001) Piter, Saint Petersburg, pp. 12-13 and 92-98.
Serafetinides, AA 'Short pulse laser beam interactions with polymers biocompatible materials and tissue' Proce SPIE vol. 3052 (1996) pp. 111-123.
Sulamanidze, M. et al., "APTOS Suture Lifting Methods: 10 Years of Experience", Clin Plastic Surg 36 (2009); pp. 281-306.
Sulamanidze, M.A. et al 'Clinical aspects of bloodless facelift using APOTS filaments' A.V. Vishnevsky Institute of Surgery, Bol'shaya Serpukhovskaya ul, 7, 113811, Moscow, Russia (2002) pp. 24-34.
Sulamanidze, M.A. et al 'Facial lifting with Aptos threads' International Journal of Cosmetic Surgery and Aesthetic Dermatology' (2001) No. 4 pp. 1-8.
Sulamanidze, M.A. et al 'Facial lifting with "Aptos" threads' http://fonendo.com (Jul. 18, 2001) pp. 1-4.
Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.
Sulamanidze, M.A. et al 'Morphological foundations of facelift using APTOS filaments' Bolshaya Serpukhovskaya ul 27, 113811 Moscow, Russia (2002) pp. 19-26.
Sulamanidze, M.A. et al 'Removal of Facial Soft Tissue Ptosis with Special Threads' Dermatol Surg (2002) vol. 28 pp. 367-371.
Sulamanidze, MD, M.A., et al., "Soft tissue lifting in the mid-face: old philosophy, new approach-internal stitching technique (APTOS NEEDLE)", Plastic and Aesthetic Surgery Clinic TOTAL SHARM, Moscow, Russia, (2005):15-29.
Sulzle, Inc. B.G. et al Drilled End Surgical Needles Jul. 2002 Syracuse, New York.
Surgical Specialties Corporation, "Wound Closure Catalog"; Summer 2005, 5 pages.
Szarmach, R. et al 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.
Tan E.L. et al., "A wireless, passive strain sensor based on the harmonic response of magnetically soft materials", Smart Materials and Structures 17 (2008): pp. 1-6.
Up Lifting (Aptos Threads), http://www.ccpr.com.br/up1-1.htm Aug. 19, 2002 pp. 1-2.
Verdan, C. 'Primary Repair of Flexor Tendons' Journal of Bone and Joint Surgery (1960) vol. 42, No. 4 pp. 647-657.
Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.
Communication from EPO re: 10000486 dated Apr. 4, 2011.
European Search Report re: EP05025816 dated Jun. 23, 2006.
European Search Report for EP07006258.3 dated May 4, 2007, 4 pages.
European Search Report for EP07015906 dated Oct. 2, 2007.
European Search Report for EP07015905.8 dated Oct. 2, 2007, 2 pages.
European Search Report for EP07016222 dated Jan. 7, 2008.
European Search Report for EP09014651 dated Jan. 12.
European Search Report for EP10000629.5 dated Mar. 10, 2010, 4 pages.
European Search Report re: EP10000486 dated Apr. 23, 2010.
European Search Report re: 10004453 dated Jun. 15, 201).
European Search Report for EP10011871.0 dated Dec. 3, 2010, 2 pages.
European Search Report for EP10011868.6 dated Dec. 6, 2010, 2 pages.
European Search Report for EP10011869 dated Jan. 20, 2011.
European Search Report for EP10186592.1 dated Jan. 19, 2011, 2 pages.
European Search Report for EP10184766 dated Apr. 20, 2011.
Extended European Search Report re: 07015905.8 dated Oct. 23, 2007.
Extended European Search Report re: 07016222.7 dated Jan. 30, 2008.
International Preliminary Examination Report re: PCT/US1998/10478 dated Dec. 11, 1999.
International Preliminary Report re: PCT/US2008/060127 dated Oct. 13, 2009.
International Preliminary Report re: PCT/US2008/087788 dated Jun. 22, 2010.
International Preliminary Report re: PCT/US2009/040545 dated Oct. 19, 2010.
International Search Report for PCT/US1994/09631 dated Dec. 9, 1994.
International Search Report for PCT/US1998/10478 dated Sep. 23, 1998.
International Search Report for PCT/US2002/027525 dated Dec. 9, 2002, 3 pages.
International Search Report for PCT/2003/30666 dated Dec. 15, 2004.
International Search Report for PCT/US2003/25088 dated Dec. 29, 2003.
International Search Report re: PCT/US2003/030674 dated Sep. 2, 2004.
International Search Report for PCT/US2005/017028 dated Mar. 26, 2008.
International Search Report for PCT/US2007/074658 dated Jun. 12, 2007, 3 pages.
International Search Report for PCT/US2008/060127 dated Sep. 23, 2008, 5 pages.
International Search Report for PCT/US2008/0064921 dated Nov. 19, 2008, 3 pages.
International Search Report for PCT/US2008/075849 dated Mar. 18, 2009, 4 pages.
International Search Report for PCT/US2009/032693 dated Aug. 26, 2009.
International Search Report for PCT/US2009/040545 dated Oct. 29, 2009.
International Search Report for PCT/US2011/035270 dated Jan. 12, 2012.
International Search Report for PCT/US2011/035271 dated Jan. 12, 2012.
International Search Report re: PCT/US2011/035431 dated Jan. 12, 2012.
International Search Report for PCT/US2011/059238 dated May 21, 2012.
Partial European Search Report re: EP05025816 dated Mar. 20, 2006.
Singapore Search Report for Singapore Patent Application No. 200702625-5 dated Nov. 26, 2008, 7 pages.

(56) References Cited

OTHER PUBLICATIONS

Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.
Supplementary European Search Report re: EP98923664 dated Jun. 12, 2001.
Supplementary European Search Report re: EP03752630 dated Nov. 17, 2005.
Supplementary European Search Report re: 03770556 dated Nov. 17, 2005.
Supplementary European Search Report re: 03754965 dated Nov. 18, 2005.
Supplementary European Search Report re: EP03785177 dated May 19, 2009.
Supplementary European Search Report re: 05750101 dated Apr. 7, 2010.
Supplementary European Search Report re: 07017663 dated Nov. 7, 2007.

* cited by examiner

APPARATUS AND METHOD FOR FORMING SELF-RETAINING SUTURES

FIELD OF INVENTION

The present invention relates generally to an apparatus and method for forming retainers in a suture and, more particularly, to an apparatus including a rotary retainer forming member for forming retainers in a suture and method thereof.

DISCUSSION OF RELATED ART

A suture is an elongated body such as, for example, a strand, filament, wire, or thread, that typically includes a needle attached or formed on at least one end. In general, sutures are used in surgical procedures to close surgical and traumatic wounds, to close the skin in plastic surgery, to secure damaged or severed tendons, muscles or other internal tissues, and in microsurgery on nerves and blood vessels. Closure of wounds and/or holding tissues together facilitates healing and re-growth.

Complications associated with knots when using conventional sutures are well known. Such complications may include: suture breakage, knot slippage, suture extrusion, infection, dehiscence and excessive inflammatory response leading to ischemia and scarring. Attempts to overcome these deficiencies with knotless sutures in the past have gained little clinical success. More recently, the development of self-retaining sutures such as, for example, self-retaining sutures, has been reported.

A self-retaining suture may be a one-way needle-drawn knotless suture which allows passage of the suture in one direction through tissue, but not in the opposite direction. A self-retaining suture may generally include a pointed leading end such as, for example, a needle, and a plurality of tissue retainers on the exterior surface of the suture. The retainers may generally be formed to collectively extend in one direction along the length of the suture. While suturing tissue, these retainers may penetrate inside the tissue and lock in place so that no knots are needed to tie the suture.

Methods of using self-retaining sutures in surgical procedures are disclosed, for example, in U.S. Pat. No. 6,599,310, entitled "Suture Method", the disclosure of which is incorporated herein by reference. Self-retaining sutures may provide the ability to put tension in the tissue with the result of less slippage of the suture in the wound. Depending on the circumstances of a given tissue repair, a given configuration of retainers on the exterior of the suture may be more preferable than another.

Various methods and apparatuses for cutting retainers on the exterior of a suture have been proposed. For example, U.S. Pat. Nos. 7,225,512, 6,848,152, and 5,931,855, each of which is hereby incorporated herein by reference in its entirety, are related to self-retaining sutures and methods for making such sutures. In general, however, these apparatuses and methods may be directed to linearly reciprocating cutting devices and the like.

SUMMARY

The apparatus and method described herein may reliably achieve a high output efficiency of self-retaining suture material based on length per second or retainers per second while providing the ability to form countless retainer configurations on the suture with one apparatus requiring limited set-up and/or changeover.

In one exemplary embodiment, an apparatus for forming retainers on a continuous strand is provided. The continuous strand may be a suture material. The apparatus may include a retainer forming member configured to rotate about a first axis. The retainer forming member may include a blade. A cutting edge of the blade may be directed substantially inward toward the first axis to define a retainer forming zone when the retainer forming member rotates about the first axis. The apparatus may further include a support member arranged adjacent to the retainer forming member and configured to receive and support the continuous strand in the retainer forming zone. When the retainer forming member rotates about the first axis the strand is intermittently or continuously cut by the cutting edge of the blade.

The retainer forming member and the support member may be moveable relative to one another to position the support member in the retainer forming zone so that the strand received and supported thereon can be cut by the blade as the retainer forming member rotates about the first axis. The support member may include a sheave configured to rotate about a second axis, such second axis being nonparallel to the first axis. Further, the second axis may be substantially perpendicular to the first axis. In addition, the retainer forming member may be movable along the first axis relative to the support member. As well, the retainer forming member may be movable along a third axis perpendicular to both the first and second axes between a first position and a second position, such that when the retainer forming member is in the first position the blade cuts retainers on the strand extending in a first direction and when the retainer forming member is in the second position the blade cuts retainers on the strand extending in a second direction opposite to the first direction. The retainer forming member may further be one of a plurality of retainer forming members disposed along a path of travel of the continuous strand, such that another retainer forming member of the plurality of retainer forming members is arranged at a different angle from the first retainer forming member about a periphery of the strand to cut the strand at a different point on the periphery of the strand.

The support member of this apparatus may be movable along the first axis relative to the retainer forming member. The support member may additionally be movable along a third axis perpendicular to both the first and second axes between a first position and a second position, such that when the support member is in the first position the blade of the retainer forming member cuts retainers on the strand extending in a first direction and when the support member is in the second position the blade of the retainer forming member cuts retainers on the strand extending in a second direction opposite to the first direction.

The apparatus may also include a feed mechanism configured to receive and support an input spool of the continuous strand such that the spool can rotate to unwind the strand from the spool, the feed mechanism being configured to rotate the spool so that the strand rotates about its own axis. In addition, the feed mechanism may be configured to twist the strand about its own axis.

The apparatus may also include a take-up mechanism configured to pull the strand from the input spool about a surface of the support member. Such take-up mechanism may be configured to receive and wind the continuous strand on an output spool after cutting. The take-up mechanism may also be configured to rotate the strand about its own axis concurrently with the feed mechanism so that the strand is not twisted between any two points along its length.

In another exemplary embodiment, a method for forming retainers on a continuous strand with the apparatus is provided. The method may include rotating the retainer forming member of the apparatus about the first axis, moving the continuous strand on the support member within the retainer forming zone, and intermittently or continuously cutting the strand with the cutting edge of the blade as the retainer forming member rotates to form retainers on the strand.

The strand may be moved by pulling the strand through the retainer forming zone about a surface of the support member with a take-up mechanism. The method may further include rotating or twisting the strand about its own axis. The continuous strand may be a suture material.

At least one of the retainer forming member or the support member may be moved relative to the other. The retainer forming member may also be moved along the first axis relative to the support member. Additionally or alternatively, the support member may be moved along the first axis relative to the retainer forming member.

The support member may include a sheave configured to rotate about a second axis which is nonparallel to the first axis. Thus the method may further include moving the retainer forming member along a third axis perpendicular to both the first and second axes to a first position, such that the cutting edge of the blade cuts retainers on the strand extending in a first direction. The method may also include moving the retainer forming member along the third axis to a second position, such that the cutting edge of the blade cuts retainers on the strand extending in a second direction opposite to the first direction.

The method may alternatively include moving the support member along a third axis perpendicular to both the first and second axes to a first position, such that the cutting edge of the blade cuts retainers on the strand extending in a first direction. This method may also include moving the support member along the third axis to a second position, such that the cutting edge of the blade cuts retainers on the strand extending in a second direction opposite to the first direction. In either case, the second axis may be substantially perpendicular to the first axis.

The support member may have a small surface area which receives and supports the strand so that the retainers formed on the strand do not contact the surface of the support member as the strand is rotated and advanced away from the retainer forming zone.

In yet another exemplary embodiment of the invention, a suture having a plurality of retainers formed on an outer periphery of a strand of suture material is provided. The suture may be formed by a method. The method may include the steps of: providing a retainer forming member configured to rotate about a first axis and comprising a blade, wherein a cutting edge of the blade is directed substantially inward toward the first axis to define a retainer forming zone when the retainer forming member rotates about the first axis; providing a support member arranged adjacent to the retainer forming member and configured to receive and support the strand of suture material in the retainer forming zone; rotating the retainer forming member about the first axis; moving the strand of suture material on the support member within the retainer forming zone; and intermittently or continuously cutting the strand of suture material with the cutting edge of the blade as the retainer forming member rotates to form a plurality of retainers on the strand of suture material. The suture may formed from an absorbable or a non-absorbable material. The strand of suture material may further be cut into individual sutures having a predetermined length.

The plurality of retainers of the suture may project in a first direction, and may be formed by moving the retainer forming member to a first position in the retainer forming zone. The plurality of retainers may further project in a second direction opposite to the first direction, and the retainers projecting in the second direction may formed by moving the retainer forming member to a second position in the retainer forming zone.

Alternatively, the plurality of retainers projecting in the first direction may formed by moving the support member to a first position in the retainer forming zone. The plurality of retainers may further project in a second direction opposite to the first direction, and retainers projecting in the second direction may be formed by moving the support member to a second position in the retainer forming zone.

The plurality of retainers cut on the outer periphery of the strand of suture material may be arranged helically along the length of the strand, and may be formed by rotating or twisting the strand about its own axis during cutting.

In yet another embodiment, an apparatus for forming retainers on a continuous strand is provided. The apparatus may include means for intermittently or continuously cutting a continuous strand; means for rotating the cutting means about a first axis to define a retainer forming zone; and means for supporting and moving the continuous strand in the retainer forming zone as the strand is cut by the cutting means. The apparatus may further include means for rotating the strand about its own axis and/or means for means for twisting the strand about its own axis.

The apparatus may further include means for moving at least one of the cutting means or the supporting and moving means relative to the other. The moving means may be configured for moving the cutting means to a first position, such that the cutting means cuts retainers on the strand extending in a first direction. The moving means may also be configured for moving the cutting means to a second position, such that cutting means cuts retainers on the strand extending in a second direction opposite to the first direction.

The moving means may be configured for moving the supporting and moving means to a first position, such that the cutting means cuts retainers on the strand extending in a first direction. As well, the moving means may be configured for moving the supporting and moving means to a second position, such that the cutting means cuts retainers on the strand extending in a second direction opposite to the first direction.

In still another embodiment, a method of forming retainers in a surgical suture is provided. The method may include unidirectionally rotating a blade about an axis to form retainers in a continuous strand of suture material, wherein the blade moves relative to the continuous strand in at least two directions while cutting each retainer. A first of the at least two directions may be approximately perpendicular to a longitudinal axis of the continuous strand and a second of the at least two directions may have a component parallel to the longitudinal axis of the strand. Further, there may be an optional third direction in which the blade moves relative to the continuous strand, the third direction being approximately perpendicular to each of the first and second directions. Further, a cutting edge of the blade substantially may point toward the axis about which the blade rotates. Alternatively, a cutting edge of the blade may substantially point away from the axis about which the blade rotates.

In yet another embodiment, a suture comprising a plurality of retainers formed on an outer periphery of a strand of suture material is provided. The suture may be formed by an apparatus comprising a retainer forming member configured to rotate about a first axis. The retainer forming member may include a blade having a cutting edge directed substantially inward toward the first axis to define a retainer forming zone when the retainer forming member rotates about the first axis.

The apparatus may further include a support member disposed adjacent the retainer forming member and configured to receive and support the strand of suture material in the retainer forming zone. The strand of suture material may be moved on the support member within the retainer forming zone and the strand of suture material may be intermittently or continuously cut by the cutting edge of the blade as the retainer forming member rotates, thereby forming a plurality of retainers on the strand of suture material.

In still another embodiment, an apparatus for cutting retainers on a continuous strand is provided. The apparatus may include a blade operable to unidirectionally and continuously rotate about an axis. A cutting edge of the blade may define a retainer forming zone when the blade rotates about the axis. The apparatus may include a support member configured to support the strand in the retainer forming zone. When the blade rotates about the axis and the support member supports the passing strand in the retainer forming zone, the blade may intermittently or continuously cut retainers on the passing strand.

In still another embodiment, a surgical suture comprising at least one retainer formed on an outer periphery of a strand of suture material is provided. The surgical suture may be formed by a method including unidirectionally rotating a blade about an axis to form at least one retainer on the outer periphery of the strand of suture material. The blade may move relative to the continuous strand in at least two directions while cutting the at least one retainer.

The details of one or more aspects or embodiments are set forth in the description below. Other features, objects and advantages will be apparent from the description, the drawings and the claims. In addition, the disclosures of all patents and patent applications referenced herein are incorporated by reference in their entirety.

BRIEF DESCRIPTION OF THE DRAWINGS

The foregoing and other features and advantages of the invention will be apparent from the following, more particular description of the exemplary embodiments of the invention, as illustrated in the accompanying drawings.

Several exemplary embodiments of the invention will be described with respect to the following drawings, in which like reference numerals represent like features throughout the figures, and in which.

DETAILED DESCRIPTION

Figure 1:
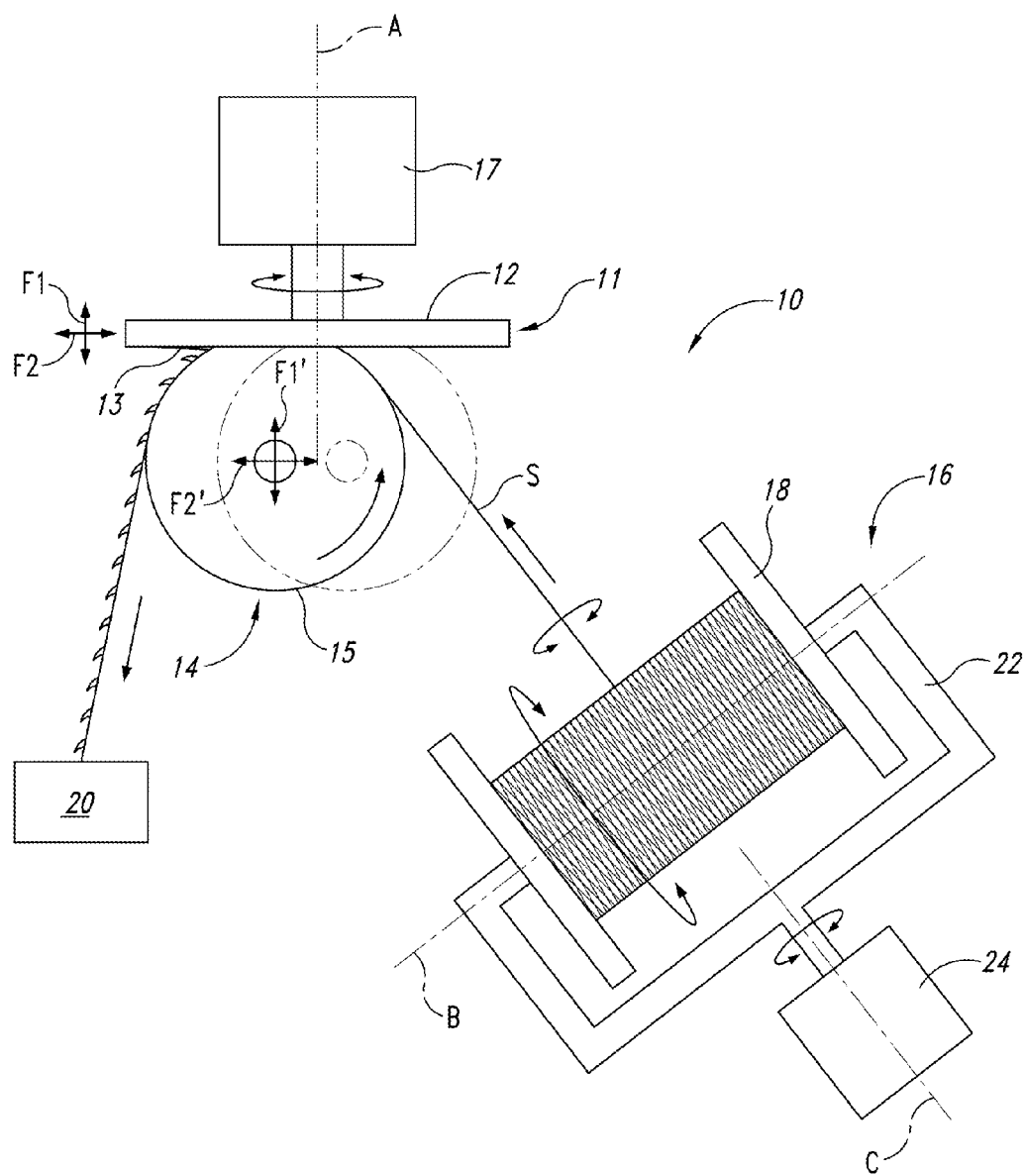
FIG. 1 is a schematic view of an apparatus for forming retainers in a continuous strand according to an embodiment of the invention.

In describing the various exemplary embodiments illustrated in the drawings, specific terminology is employed for the sake of clarity. However, the invention is not intended to be limited to the specific terminology so selected. It is to be understood that each specific element includes all technical equivalents that operate in a similar manner to accomplish a similar purpose.

In the following description of certain embodiments of the invention, directional words such as "top," "bottom," "upwardly," and "downwardly" are employed by way of description and not limitation with respect to the orientation of the apparatus and its various components as illustrated in the drawings. Similarly, directional words such as "axial" and "radial" are also employed by way of description and not limitation.

EXEMPLARY DEFINITIONS

The term "tissue retainer" (and variations thereof such as, for example, "retainer" or "barb") as used herein, may refer to a point or pointed part projecting from a strand such as, for example, a suture element having a retainer body projecting from the suture body and a retainer end adapted to penetrate tissue. Each retainer is adapted to resist movement of the suture in a direction other than the direction in which the suture is deployed into the tissue by the surgeon, by being oriented to substantially face the deployment direction (i.e. they lie flat when pulled in the deployment direction; and open or "fan out" when pulled in a direction contrary to the deployment direction). As the tissue-penetrating end of each retainer faces away from the deployment direction when moving through tissue during deployment, the tissue retainers should not catch or grab tissue during this phase. Once the self-retaining suture has been deployed, a force exerted in another direction (often substantially opposite to the deployment direction) causes the retainers to be displaced from their deployment positions (i.e. resting substantially along the suture body), forces the retainer ends to open (or "fan out") from the suture body in a manner that catches and penetrates into the surrounding tissue, and results in tissue being caught between the retainer and the suture body; thereby "anchoring" or affixing the self retaining suture in place.

The term "retainer configurations" (and variations thereof such as, for example, but not limited to "barb configurations") may refer to configurations of tissue retainers and can include features such as size, shape, surface characteristics, and so forth.

The term "blade" (and variations thereof), as used herein, may refer to the cutting part of a sharpened tool or member.

The term "continuous" (and variations thereof), as used herein, may mean substantially uninterrupted in time, sequence, substance, or extent.

The term "sheave" (and variations thereof), as used herein, may refer to a wheel or disk with a grooved rim. A non-limiting example of a sheave may include a pulley.

The term "spool" (and variations thereof), as used herein, may refer to any member or device on which something is wound.

The term "strand" (and variations thereof), as used herein, may refer to a thin elongated cord, thread, or filament of natural or synthetic material.

The term "suture" (and variations thereof), as used herein, may refer to an elongated body such as, for example, but not limited to, a strand, filament, wire, thread, or other material to be used surgically to close a wound or join tissues.

The term "transition segment" (and variations thereof such as, for example, but not limited to "transition portion") may refer to a retainer-free (barb-free) portion of a suture such as, for example, the portion on a bi-directional suture located between a first set of retainers oriented in one direction and a second set of retainers oriented in another direction.

The term "suture thread" may refer to the filamentary body component of a suture, and, for sutures requiring needle deployment, does not include the suture needle. The suture thread may be monofilamentary, or, multifilamentary.

The term "monofilament suture" may refer to a suture comprising a monofilamentary suture thread.

The term "braided suture" may refer to a suture comprising a multifilamentary suture thread. The filaments in such suture threads are typically braided, twisted, or woven together.

The term "self-retaining suture" (and variations thereof such as, for example, but not limited to, "barbed suture") may refer to a suture that does not require a knot or a suture anchor at its end in order to maintain its position into which it is deployed during a surgical procedure. "Self-retaining suture" may refer to a suture with one or more retainers located along the suture. The retainers may be of sufficient size and appropriate geometry for fastening to, or gripping, tissue through which the self-retaining suture is inserted and achieving closure of an incision or wound (or repositioning tissue) with superior attachment or without the need for tying knots. Retainers may be configured to have tissue insertion points (such as, for example, barbs), tissue insertion edges (such as conical or frusto-conical retainers), and so forth. These sutures may be monofilament sutures or braided sutures, and are positioned in tissue in two stages, namely deployment and affixation, and include at least one tissue retainer.

The term "retainer forming member" as used herein may include cutters such as blades, grinding wheels, cutting discs, and lasers (both cutting and vaporising lasers).

The term "one-way self-retaining suture" (and variations thereof such as, for example, but not limited to "one-directional suture," "one-directional self-retaining suture," "one-way suture," "uni-directional self-retaining suture," or "uni-directional suture") may refer to a suture having retainers (e.g., barbs) on its exterior surface and facing towards one end of the suture. Such arrangement of retainers on the suture may allow the suture to be drawn in only one direction through tissue, but not in the opposite direction.

The term "two-way self-retaining suture" (and variations thereof such as, for example, but not limited to "two-way suture," "two-directional self-retaining suture," "two-directional suture," "bi-directional self-retaining suture," or "bi-directional suture") may refer to a suture that has retainers (e.g., barbs) facing toward one end of the suture over a portion of the suture length and retainers (e.g., barbs) facing the opposite direction toward the other end of the suture over another portion of the suture length. This arrangement may allow the retainers to move in the same direction as each respective suture end is inserted into host tissue. A bi-directional suture may typically be armed with a needle at each end of the suture thread. Many bi-directional sutures may have a transitional segment located between the two retainer orientations.

The term "absorbable" (and variations thereof such as, for example, but not limited to, "degradable" or "biodegradable" or "bioabsorbable") may refer to materials for which an erosion or degradation process is at least partially mediated by, or performed in, a biological system. An absorbable suture may refer to a suture which, after introduction into a tissue is broken down and absorbed by the body. Typically, the degradation process is at least partially mediated by, or performed in, a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination or these) or by a thermal or photolytic process. Polymer degradation may be characterized, for example, using gel permeation chromatography (GPC), which monitors the polymer molecular mass changes during erosion and breakdown. Degradable suture material may include polymers such as polyglycolic acid, copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). These sutures can be in either a braided multifilament form or a monofilament form. The polymers used in the present invention can be linear polymers, branched polymers or multi-axial polymers. Examples of multi-axial polymers used in sutures are described in U.S. Patent Application Publication Nos. 20020161168, 20040024169, and 20040116620. Sutures made from degradable suture material lose tensile strength as the material degrades.

The term "non-absorbable" (and variations thereof such as, for example, but not limited to, "non-degradable" or "non-biodegradable" or "non-bioabsorbable") may refer to material for a suture that is not degraded by chain scission such as chemical reaction processes (e.g., hydrolysis, oxidation/reduction, enzymatic mechanisms or a combination or these) or by a thermal or photolytic process. Non-degradable suture material includes polyamide (also known as nylon, such as nylon 6 and nylon 6.6), polyester (e.g., polyethylene terephthalate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethelene, silk, and cotton. Sutures made of non-degradable suture material are suitable for applications in which the suture is meant to remain permanently or is meant to be physically removed from the body.

The term "suture diameter" may refer to the diameter of the body of the suture. It is to be understood that a variety of suture lengths may be used with the sutures described herein and that while the term "diameter" is often associated with a circular periphery, it is to be understood herein to indicate a cross-sectional dimension associated with a periphery of any shape. Suture sizing is typically based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. The actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0.

The term "suture deployment end" may refer to an end of the suture to be deployed into tissue; one or both ends of the suture may be suture deployment ends. The suture deployment end may be attached to deployment means such as a suture needle, or may be sufficiently sharp and rigid to penetrate tissue on its own.

DETAILED DESCRIPTION OF EXEMPLARY EMBODIMENTS

FIG. 1 is a schematic view of an apparatus for forming retainers in a continuous strand according to an exemplary embodiment of the invention. The apparatus 10 may include a retainer forming member 11 and a support member 14 arranged adjacent to one another. The retainer forming member 11 may be arranged to be rotatably driven about an axis A by a first rotary drive device 17 (e.g., an electric, pneumatic, hydraulic, or magnetic servo motor) and may include a main body 12 and a blade 13 attached to the main body 12. The blade 13 may have a cutting edge directed substantially inward toward the axis A. A feed mechanism 16 may be arranged to support an input spool 18 which supplies a continuous strand of material S to the support member 14 such that the retainer forming member 11 can form retainers on the strand S. A take-up mechanism 20 may be arranged to pull the continuous strand S from the input spool 18 about an outer surface of the support member 14.

In the embodiment depicted in FIG. 1, the continuous strand S is shown wound about the input spool 18. The input spool 18 may be supported by a frame 22 such that the input spool 18 is freely rotatable about an axis B to allow the strand S to be unwound therefrom. The frame 22 may also be arranged to be rotatably driven about another axis C by a second rotary drive device 24 (e.g., an electric, pneumatic, hydraulic, or magnetic servo motor). In FIG. 1, axis C is shown as being perpendicular to the axis B. When the second rotary drive device 24 rotates the frame 22 about axis C, the strand S may be twisted about its own axis as it is unwound from the input spool 18.

In operation, rotary drive device 24 may rotate the frame 22 about axis C while strand S is pulled by take-up mechanism 20. Strand S may unwind from the input spool 18 in a helically twisted state and may be received and supported on an outer surface 15 of the support member 14 as it travels toward the take-up mechanism 20. In the embodiment shown in FIG. 1, support member 14 may be a sheave which is rotatable about an axis extending perpendicular to the axis A. The outer surface 15 of the support member 14 may include a channel or groove (not shown) for receiving the strand S.

The retainer forming member 11 and the support member 14 may be moveable relative to one another in at least two directions. For example, retainer forming member 11 may be moveable in one or both of directions F1 and F2 as shown in FIG. 1 to position the passing strand S such that retainers can be continuously or intermittently formed thereon by the blade 13 of the retainer forming member 11 during rotation of the retainer forming member 11 about axis A. Alternatively, support member 14 may be moveable in one or both of directions F1' and F2' as shown in FIG. 1 to position the passing strand S such that retainers can be continuously or intermittently formed thereon by the blade 13 of the retainer forming member 11 during rotation of the retainer forming member 11 about axis A. Thus, although the support member 14 is shown in FIG. 1 as having an alternative position relative to the retainer forming member 11 (denoted by a dotted outline), either one of the retainer forming member 11 and support member 12 may move relative to the other to position the strand S as necessary for cutting. As will be discussed in greater detail below with reference to FIGS. 2A, 2B, 3A, 3B, 4A, and 4B, such relative movement may provide the apparatus 10 with the ability to engage and disengage the blade 13 from contact with the strand S as well as vary the depth and angle of cut and the retainer direction (i.e., left-hand retainer versus right-hand retainer). Additionally, any relative motion changing the depth of the cut can be used, such as, for example, moving the retainer forming member 12 or support member 15 along an axis extending into or out of the page according to the view shown in FIG. 1. The angle of cut may be changed, for example, by moving the retainer forming member 12 along axis A and re-adjusting the depth of cut. In general, the members 12 and 15 can be moved in many degrees of freedom relative to one another to achieve different cutting properties.

As can be seen in FIG. 1, the take-up mechanism 20 may be positioned downstream of the retainer forming member 11 and the support member 14 based on the direction of flow of the strand S. Although shown generically in FIG. 1, the take-up mechanism 20 may be, for example, an output spool arranged to wind the strand S thereon or it may be another processing device such as, for example, a mechanism which gathers the strand S and severs the continuous strand S at predetermined length intervals. The apparatus 10 can also be coupled to another unit down the production line such as, for example, a machine configured to crimp needles to the strand S.

Figure 2A:
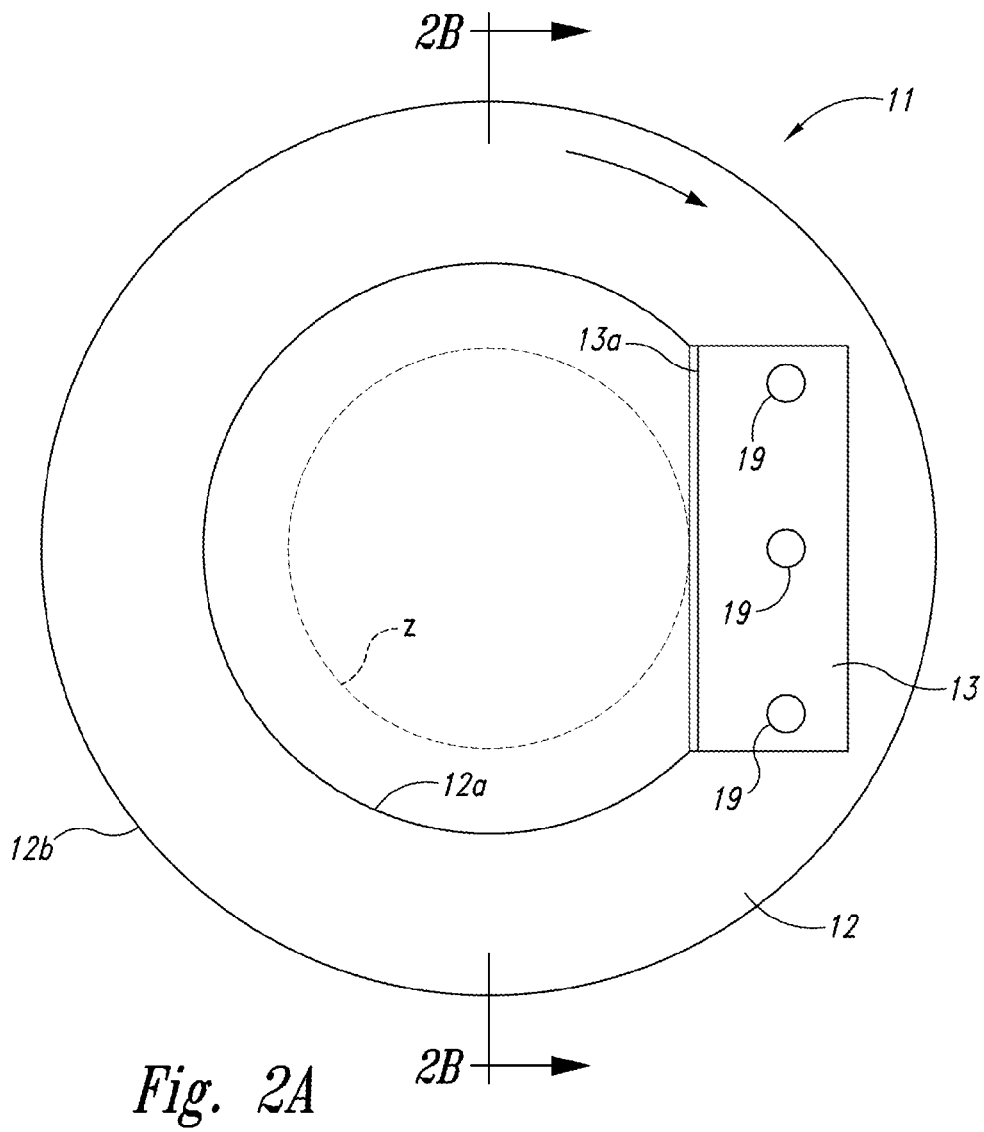
FIG. 2A is a schematic bottom view of the retainer forming member according to the embodiment shown in FIG. 1.
Figure 2B:
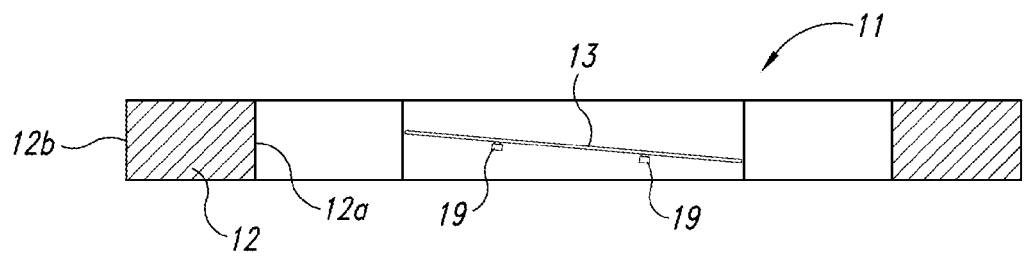
FIG. 2B is a cross-sectional side view of the retainer forming member of FIG. 2A taken through line 2B-2B.

FIGS. 2A and 2B depict schematic bottom and side cross-sectional views of the retainer forming member 11. The main body 12 of the retainer forming member 11 is depicted as a circular ring having an inner annular surface 12a and an outer annular surface 12b. The blade 13 may be attached to the main body 12. In FIGS. 2A and 2B, the blade 13 is shown as being attached via fasteners 19 (e.g., bolts or screws) but one of skill in the art will recognize that other suitable attachment measures may be used such as, for example, but not limited to, welding, adhesive, snap fit, friction fit, and the like. Alternatively, the blade 13 could be integrally formed on the main body 12. The blade 13 may have a cutting edge 13a directed substantially radially inward such that, when the retainer forming member 11 is rotating, the cutting edge 13a of the blade 13 defines a retainer forming zone Z. Although the blade 13 is shown as having a flat cutting edge 13a, it will be apparent that cutting edge 13a could take on a variety of other configurations (not shown) including, for example, but not limited to, straight, curved, stepped, slanted, etc. Furthermore, the cutting edge 13a of blade 13 can extend linearly across a portion of the area defined by the inner surface 12a as shown in FIGS. 2A and 2B but may also be formed as a continuous or intermittent annular cutting edge (not shown) which extends inward from the inner surface 12a. A continuous helical retainer about the outer surface of the strand S may be cut by a rotating blade making continuous contact with the suture so long as the pitch is very tight, e.g., thread-like, or by keeping the blade stationary and rotating the strand S at high speed, similar to thread cutting on a lathe. Additionally, the angle of the blade 13 with respect to the plane of rotation of the retainer forming member 11 may vary to provide different types of cutting action and, as a result, differently shaped retainers as may be desired.

The blade 13 is shown in FIG. 2B as being tilted relative to the plane or rotation. This configuration may provide desired lifting action as the blade 13 contacts and slices through the strand S as each retainer is cut. In effect, the cutting point is lifted or changed as blade 13 rotates (by as much as, for example, 1-2 mm). This lifting action can be important for materials such as, for example, lower modulus suture material, in which a formed retainer may tend to close back against the body of the strand S after cutting.

Figure 3A:
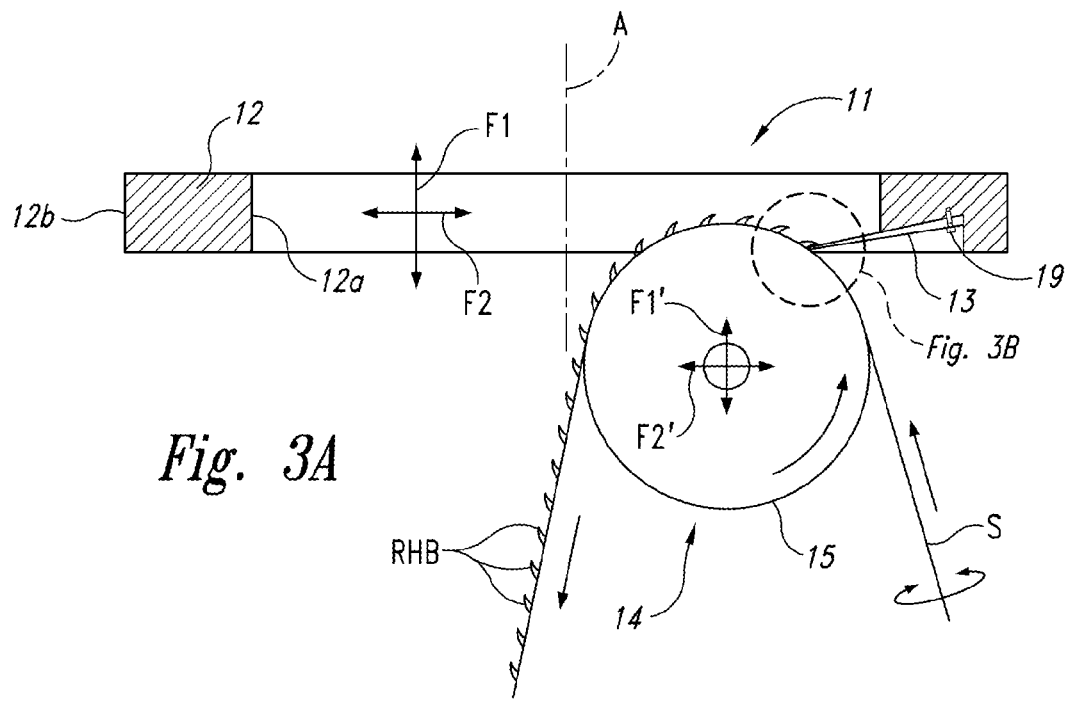
FIG. 3A is a cross-sectional side view of the retainer forming member shown in FIG. 1 with the support member shown in a first operational position within the retainer forming zone.
Figure 3B:
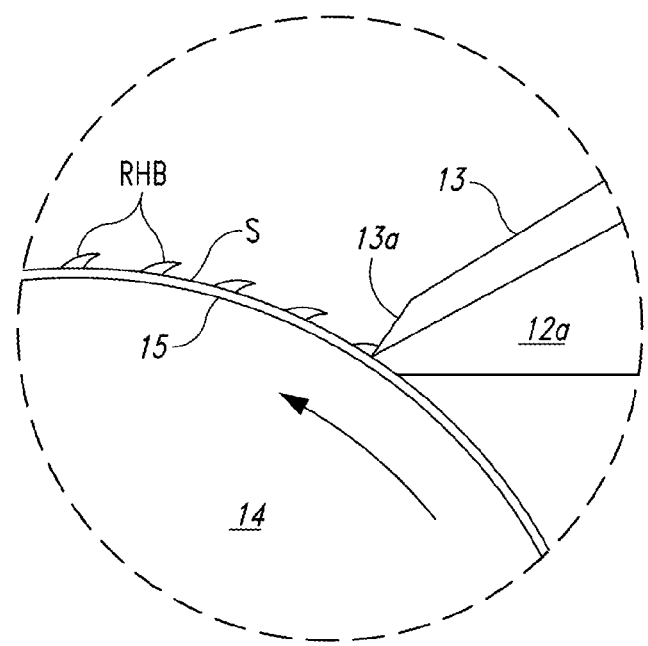
FIG. 3B is a detailed view of the retainer forming member and the support member according to the embodiment shown in FIG. 3A.

FIG. 3A is a cross-sectional side view of the retainer forming member 11 with the support member 14 shown in a first operational cutting position within the retainer forming zone Z to form right-handed retainers RHB on the helically twisted passing continuous strand S with blade 13 as the retainer forming member 12 rotates about axis A. FIG. 3B is a detailed view of the retainer forming member 11 and the support member 14 according to the embodiment shown in FIG. 3A.

In order to achieve good cutting action the blade 13 may be positioned to simultaneously slide across the strand S as it penetrates the strand S during rotation to define a smooth slicing motion. If this is not done, the cutting action can be poor and the blade can dull rapidly, as cutting is done by a single point on the blade. In order to achieve high speed, the retainer forming member 12 may rotate in unidirectional rotary motion about axis A. Any reciprocation motion (linear or rotational) may induce vibration, larger forces, and, as a result, operational speed may be limited.

Figure 4A:
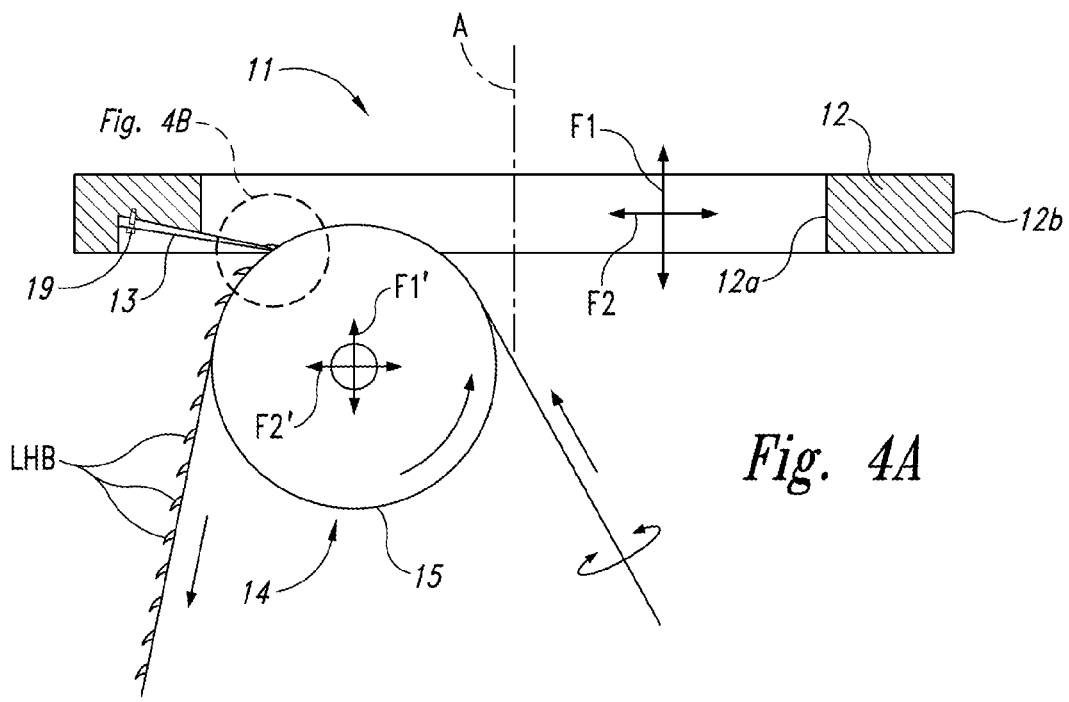
FIG. 4A is a cross-sectional side view of the retainer forming member shown in FIG. 1 with the support member shown in a second operational position within the retainer forming zone.
Figure 4B:
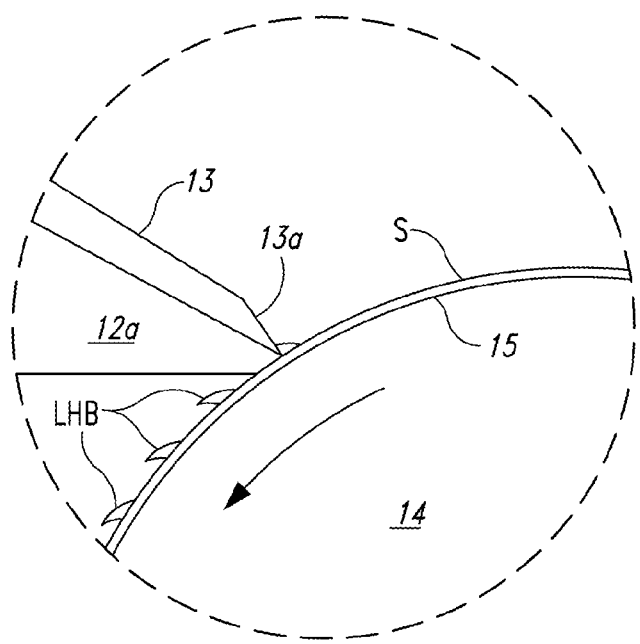
FIG. 4B is a detailed view of the retainer forming member and the support member according to the embodiment shown in FIG. 4A.

FIG. 4A is a cross-sectional side view of the retainer forming member 11 with the support member 14 shown in a second operational cutting position within the retainer forming zone Z to form left-handed retainers LHB on the helically twisted passing continuous strand S with blade 13 as the retainer forming member 12 rotates about axis A. FIG. 4B is a detailed view of the retainer forming member 11 and the support member 14 according to the embodiment shown in FIG. 4A.

Figure 5:
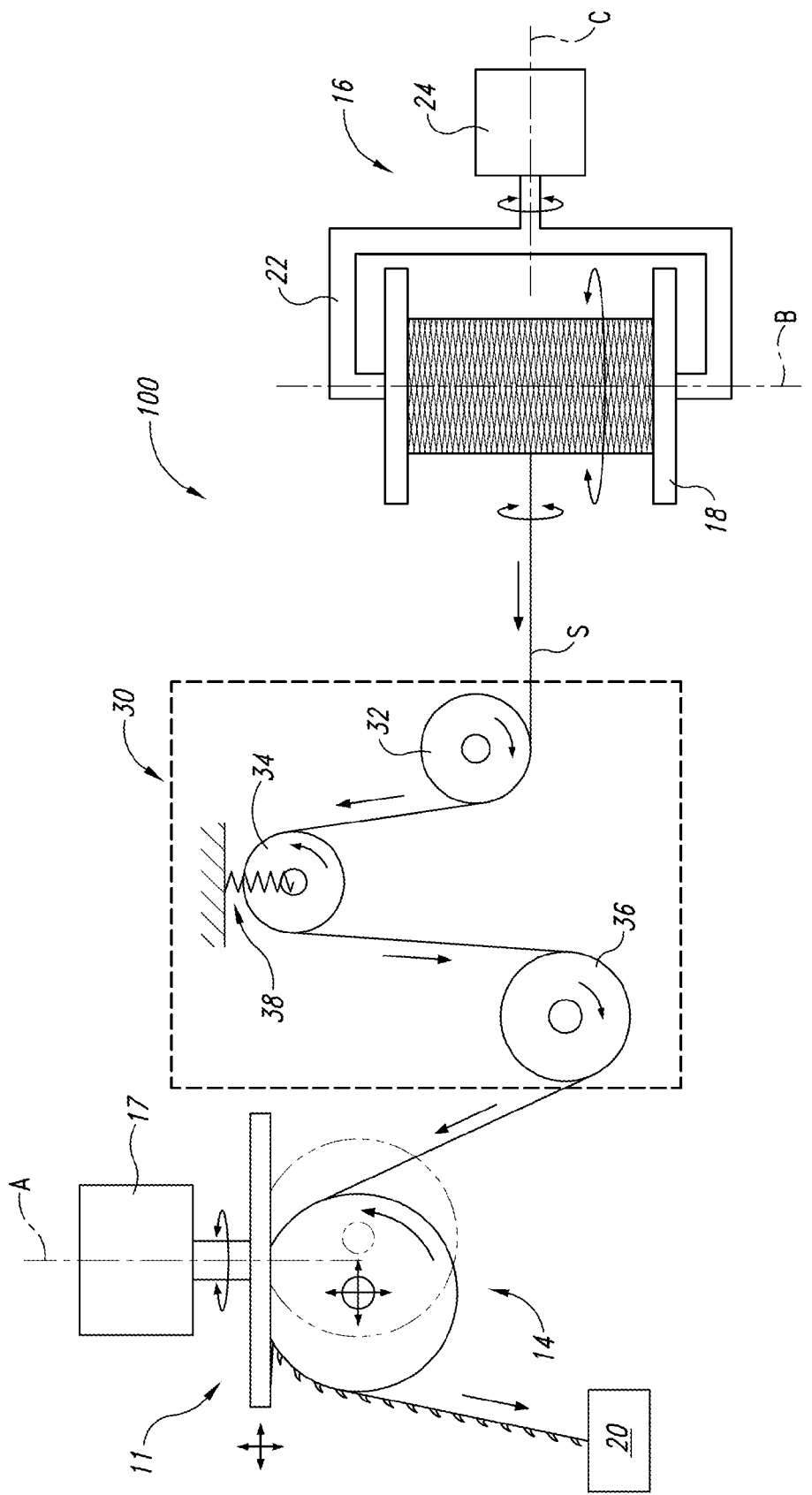
FIG. 5 is a schematic view of the apparatus for forming retainers in a continuous strand according to the embodiment shown in FIG. 1 including a strand tension maintenance mechanism.

FIG. 5 is a schematic view of an apparatus 100 for forming retainers in a continuous strand S according to another embodiment of the invention. The apparatus 100 is the same as the embodiment shown in FIG. 1 except that the apparatus 100 may additionally include a strand tension maintenance mechanism 30 positioned between the feed mechanism 16 and the cutting and support members 11, 14 along the path of travel of the continuous strand S. As shown in FIG. 5, a plurality of intermediate sheaves or pulleys 32, 34, 36 may be disposed at offset positions along the path of travel of the continuous strand S to regulate tension in the strand S as it travels to the support member 14. A constant tension device 38 which may be, for example, a spring, may couple one of the intermediate sheaves, e.g., sheave 34, to a stationary frame or body to provide constant tension in the strand S. Tensioning devices such as, for example, springs, magnetic particle brakes, electric motors, mechanical friction brakes, eddy current brakes, hysteresis brakes, and the like, are well known in the art and will not be described further herein.

In the previously described embodiments of FIGS. 1-5, the continuous strand S can be helically twisted about its own axis by rotary drive device 24 such that when the blade 13 of the retainer forming member 11 cuts retainers into the passing continuous strand S along a line extending parallel to the axis of the strand S, the strand S can then be untwisted so that the retainers formed thereon may extend along the length of the strand S in a helical configuration.

Figure 6:
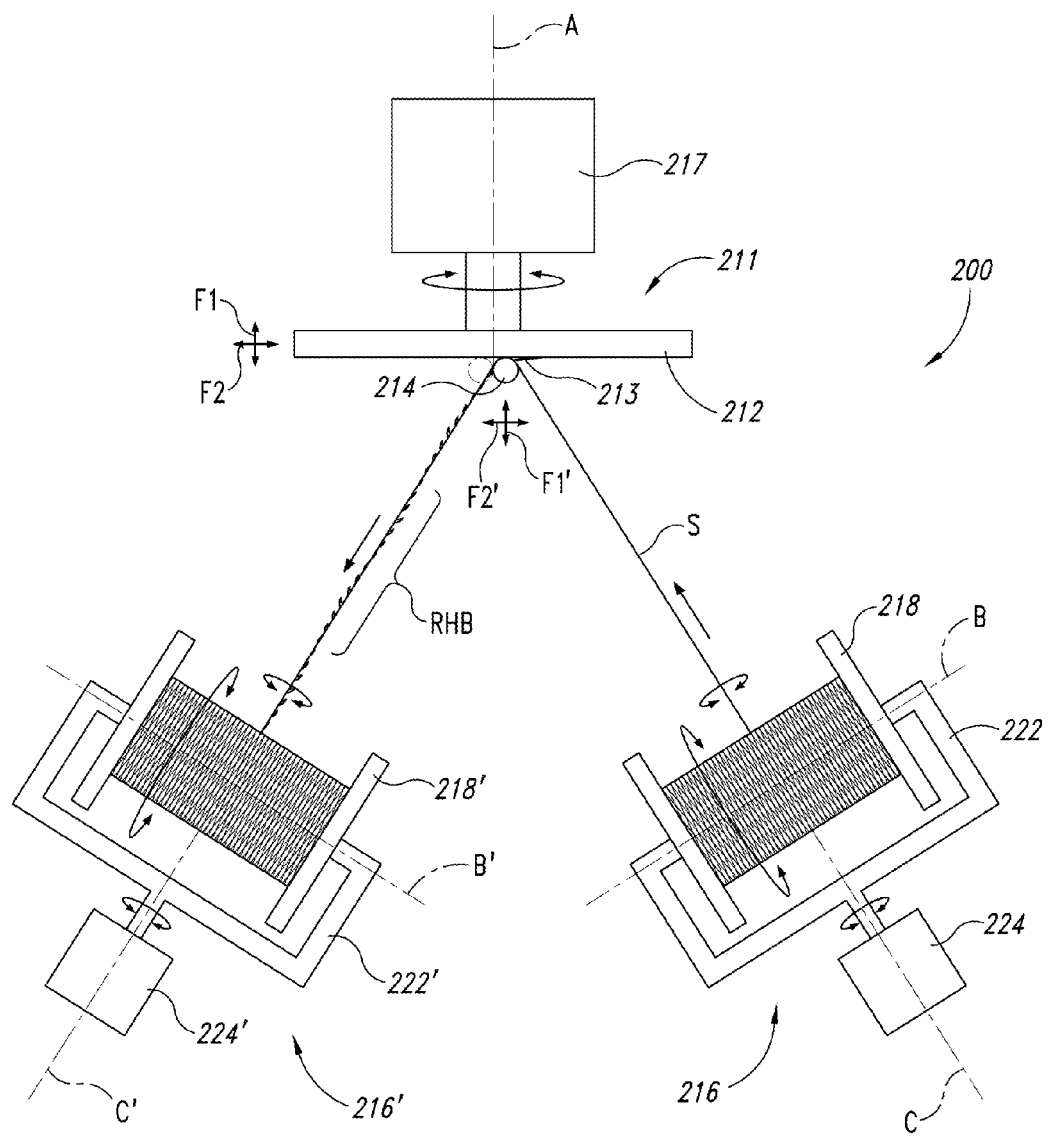
FIG. 6 is a schematic view of the apparatus for forming retainers in a continuous strand according to yet another embodiment of the invention.

FIG. 6 is a schematic view of an apparatus 200 for forming retainers in a continuous strand S according to yet another embodiment of the invention wherein the strand S is not helically twisted about its own axis but, rather, is uniformly rotated about its own axis along its entire exposed length. In this regard, any deleterious effects on the strand S due to twisting such as, for example, cracking, splitting, strain hardening, delamination, and the like, may be alleviated.

In the embodiment depicted in FIG. 6, a feed mechanism 216 may be provided having an input spool 218 freely rotatable about axis B and supported by frame 222. Frame 222 may be arranged to be rotatably driven about axis C by rotary drive device 224 (e.g., an electric, pneumatic, hydraulic, or magnetic servo motor), wherein axis C is shown as being perpendicular to axis B. Likewise, a take-up mechanism 216' may be provided having an output spool 218' freely rotatable about axis B' and supported by frame 222'. Frame 222' may be arranged to be rotatably driven about axis C' by rotary drive device 224' (e.g., an electric, pneumatic, hydraulic, or magnetic servo motor), wherein axis C' is shown as being perpendicular to axis B'. The feed mechanism 216 and take-up mechanism 216' may be configured to rotate concurrently in a predetermined direction as the strand S is pulled from the input spool 218 by the output spool 218' so that the strand S uniformly rotates about its own axis along its length to avoid twisting.

Figure 7:
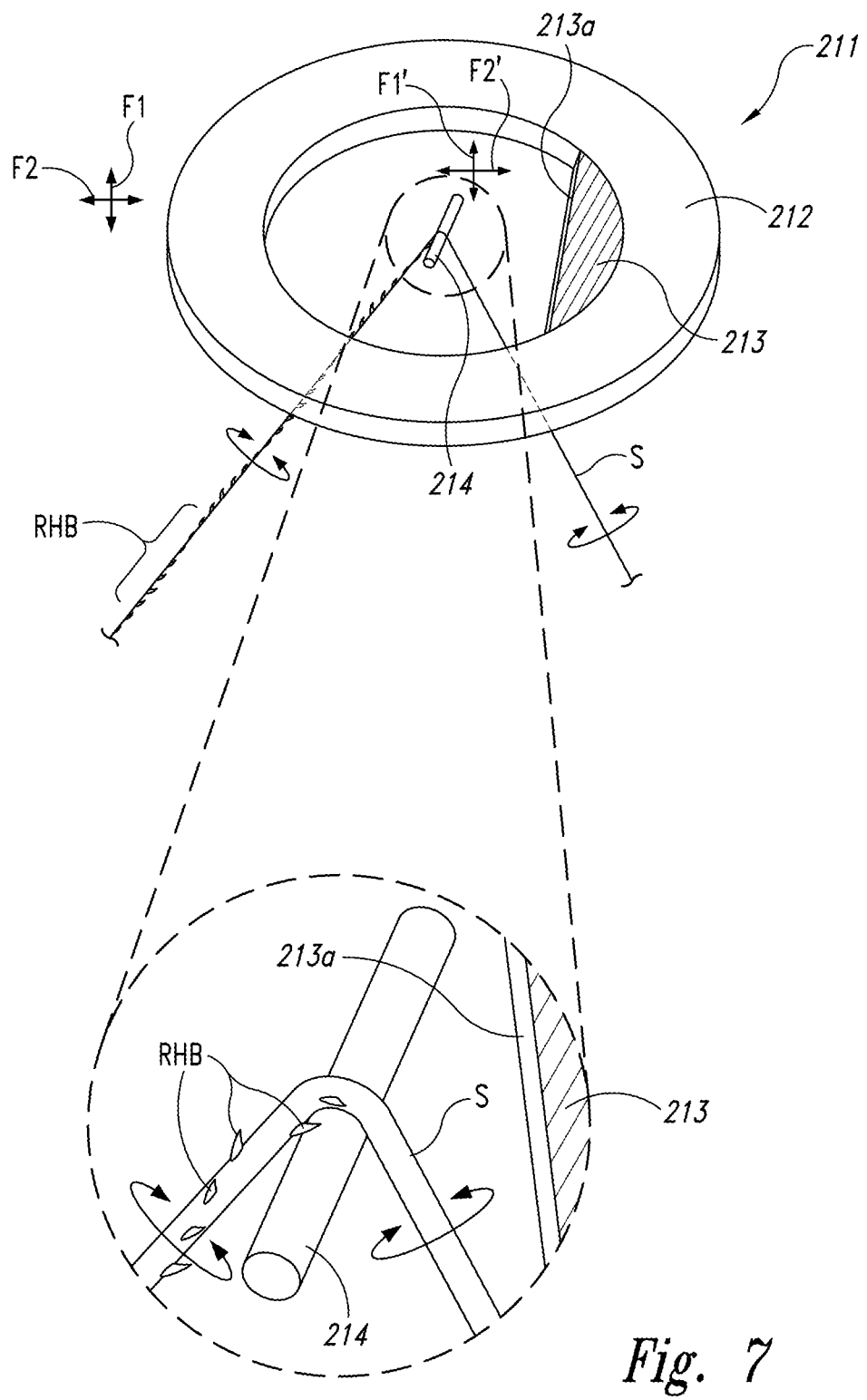
FIG. 7 is an illustrative perspective view of the apparatus in FIG. 6.

Still referring to FIG. 6, the apparatus 200 may include a retainer forming member 211 arranged to be rotatably driven about an axis A by rotary drive device 217 (e.g., an electric, pneumatic, hydraulic, or magnetic servo motor). The retainer forming member 211 may include a main body 212 and a blade 213 attached to or integrally formed on the main body 212 having a cutting edge 213a directed substantially inward toward axis A. A support member 214 may be provided adjacent to the retainer forming member 211 and within a retainer forming zone Z. As described above with regard to the embodiment depicted in FIGS. 1-4, the retainer forming member 211 and support member 214 shown in FIG. 6 may be moveable relative to one another. The strand S may be received and supported on an outer surface of the support member 214 as the strand S passes from input spool 218 to output spool 218'. The outer surface of support member 214 in this embodiment may have a relatively small surface area to receive and support the strand S in the retainer forming zone Z such that, when the blade 213 cuts right-handed retainers RHB on the passing strand S, the retainers RHB do not contact the outer surface of the support member 214 as the strand S rotates about its own axis. FIG. 7 depicts a more detailed illustrative perspective view of the apparatus 200 in FIG. 6 showing the strand S as it passes over the support member 214 while right-handed retainers RHB are cut by the blade 213. In the detailed view shown in FIG. 7, the retainers RHB may not contact the outer surface of the support member 214 as the passing strand S rotates about its own axis.

Figure 8:
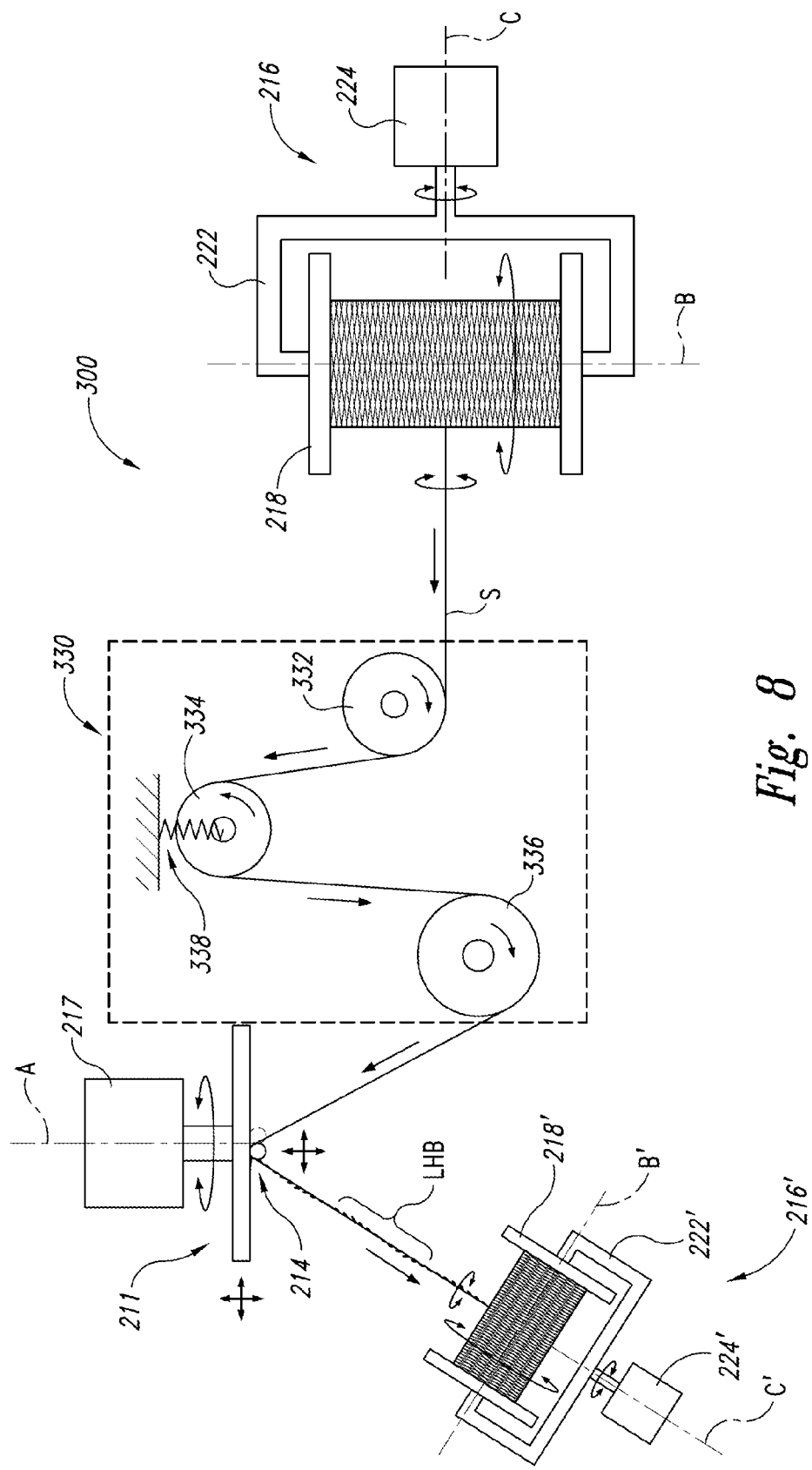
FIG. 8 is a schematic view of the apparatus for forming retainers in a continuous strand according to the embodiment shown in FIG. 6 including a strand tension maintenance mechanism.

FIG. 8 is a schematic view of an apparatus 300 for forming retainers in a continuous strand S according to another embodiment of the invention. The apparatus 300 is the same as the embodiment shown in FIG. 6 except that the apparatus 300 may additionally include a strand tension maintenance mechanism 330 positioned between the feed mechanism 216 and the cutting and support members 211, 214 along the path of travel of the continuous strand S. As shown in FIG. 8, a plurality of intermediate sheaves or pulleys 332, 334, 336 may be disposed at offset positions along the path of travel of the continuous strand S to regulate tension in the strand S as it travels to the support member 214. A constant tension device 338 which may be, for example, a spring, may couple one of the intermediate sheaves, e.g., sheave 334, to a stationary frame or body to provide constant tension in the strand S. Support element 214 is also shown in a position relative to the retainer forming member 211 such that left-handed retainers LHB may be cut on the passing continuous strand S.

Figure 9:
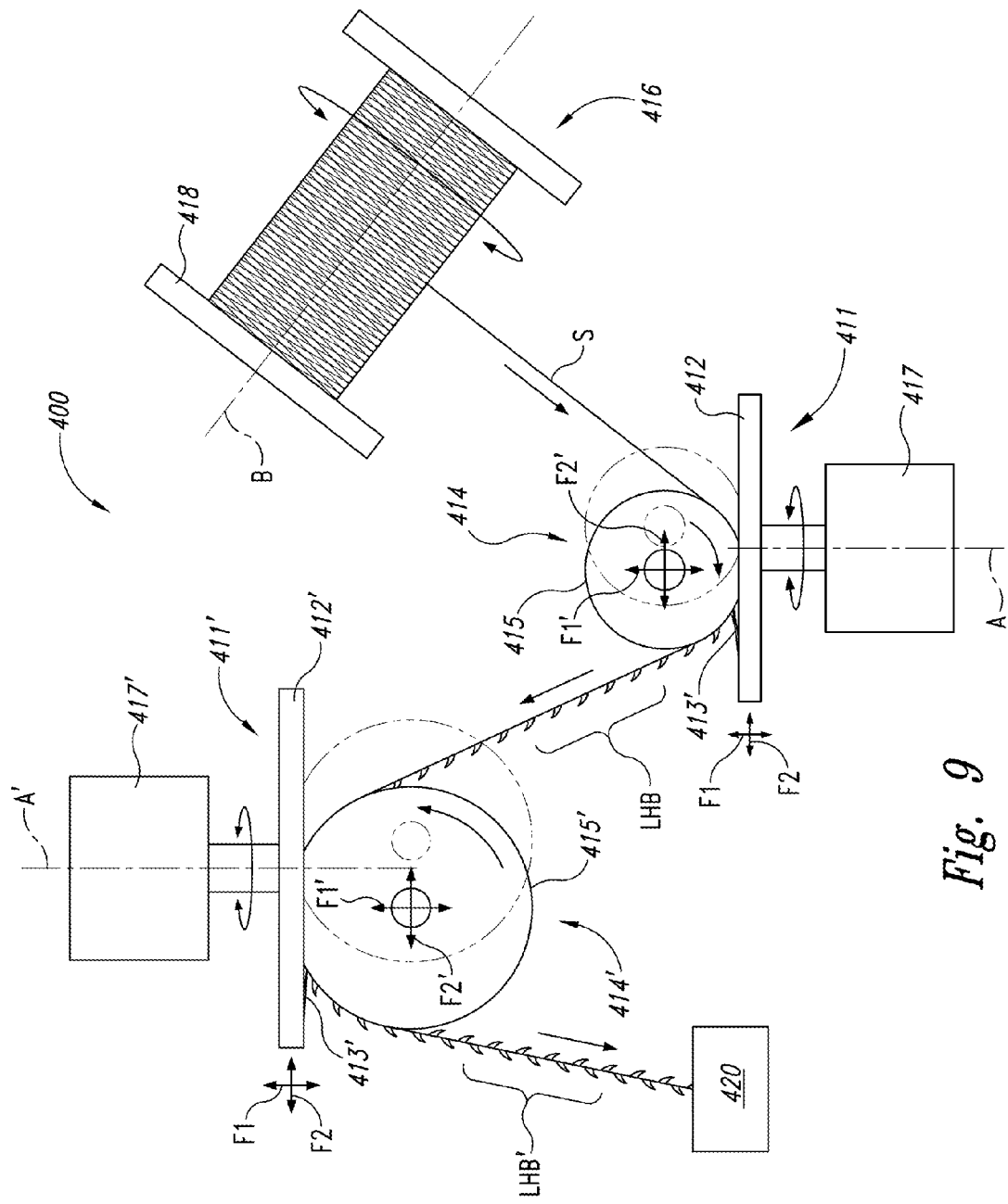
FIG. 9 is a schematic view of the apparatus for forming retainers in a continuous strand according to still another embodiment of the invention.

FIG. 9 is a schematic view of an apparatus 400 for forming retainers in a continuous strand S according to still another embodiment of the invention. A feed mechanism 416 may be provided which may include an input spool 418 about which a continuous strand S is wound. Input spool 418 may be arranged to freely rotate about an axis B as strand S is pulled by a take-up mechanism 420. In the embodiment depicted in FIG. 9, the strand S may not be rotated or twisted about its own axis. Instead, a plurality of support members 414, 414' and retainer forming members 411, 411' may be disposed between the feed mechanism 416 and the take-up mechanism 420 along a path of travel of the strand S and at differing circumferential positions about the strand S to cut retainers along and around the exterior of strand S. For example, as shown in FIG. 9, as strand S is unwound from input spool 418 it may be received and supported on an outer surface 415 of a support element 414 which may be disposed adjacent to a retainer forming member 411. The retainer forming member 411 may include a main body 412 and a blade 413 having a cutting edge directed substantially inward toward an axis A about which the retainer forming member 411 is rotatably driven by rotary drive device 417 (e.g., an electric, pneumatic, hydraulic, or magnetic servo motor). The support member 414 and retainer forming member 411 may be moveable relative to one another. In the embodiment shown in FIG. 9, the support member 414 and retainer forming member 411 may be positioned such that the blade 413 can cut left-handed retainers LHB axially along the exterior surface of the strand S.

After passing over support member 414 and being cut by retainer forming member 211, the strand S may travel toward and may be received and supported on the outer surface 415' of another support member 414' which may be disposed adjacent to another retainer forming member 411'. The additional retainer forming member 411' may include a main body 412' and a blade 413' having a cutting edge directed substantially inward toward an axis A' about which the retainer forming member 411' may be rotatably driven by rotary drive device 417' (e.g., an electric, pneumatic, hydraulic, or magnetic servo motor). The support member 414' and retainer forming member 411' may be moveable relative to one another. In the embodiment shown in FIG. 9, the support member 414' and retainer forming member 411' are positioned such that the blade 413' can cut another set of left-handed retainers LHB' axially along the exterior surface of the strand S at a different circumferential position about the strand S than the line of retainers LHB cut by the retainer forming member 411. In this way, two circumferentially spaced lines of retainers may be formed along the length of strand S.

Although FIG. 9 only shows two retainer forming members 411, 411' and two support members 414, 414' disposed between the feed mechanism 416 and the take-up mechanism 420 along a path of travel of the strand S at differing circumferential positions about the strand S, one of skill in the art will recognize that any number of corresponding retainer forming member and support member combinations may be disposed along the path of travel of the strand S at additional differing circumferential positions about the strand S to cut retainers along and around the exterior of strand S. Finally, in FIG. 9, take-up mechanism 420 may be positioned downstream of the retainer forming members 411, 411' and the support members 414, 414' based on the direction of flow of the strand S. Although shown generically in FIG. 9, the take-up mechanism 420 may be, for example, an output spool arranged to wind the strand S thereon or it may be another processing device such as, for example, a mechanism which gathers the strand S and severs the continuous strand S at predetermined length intervals.

Figure 10:
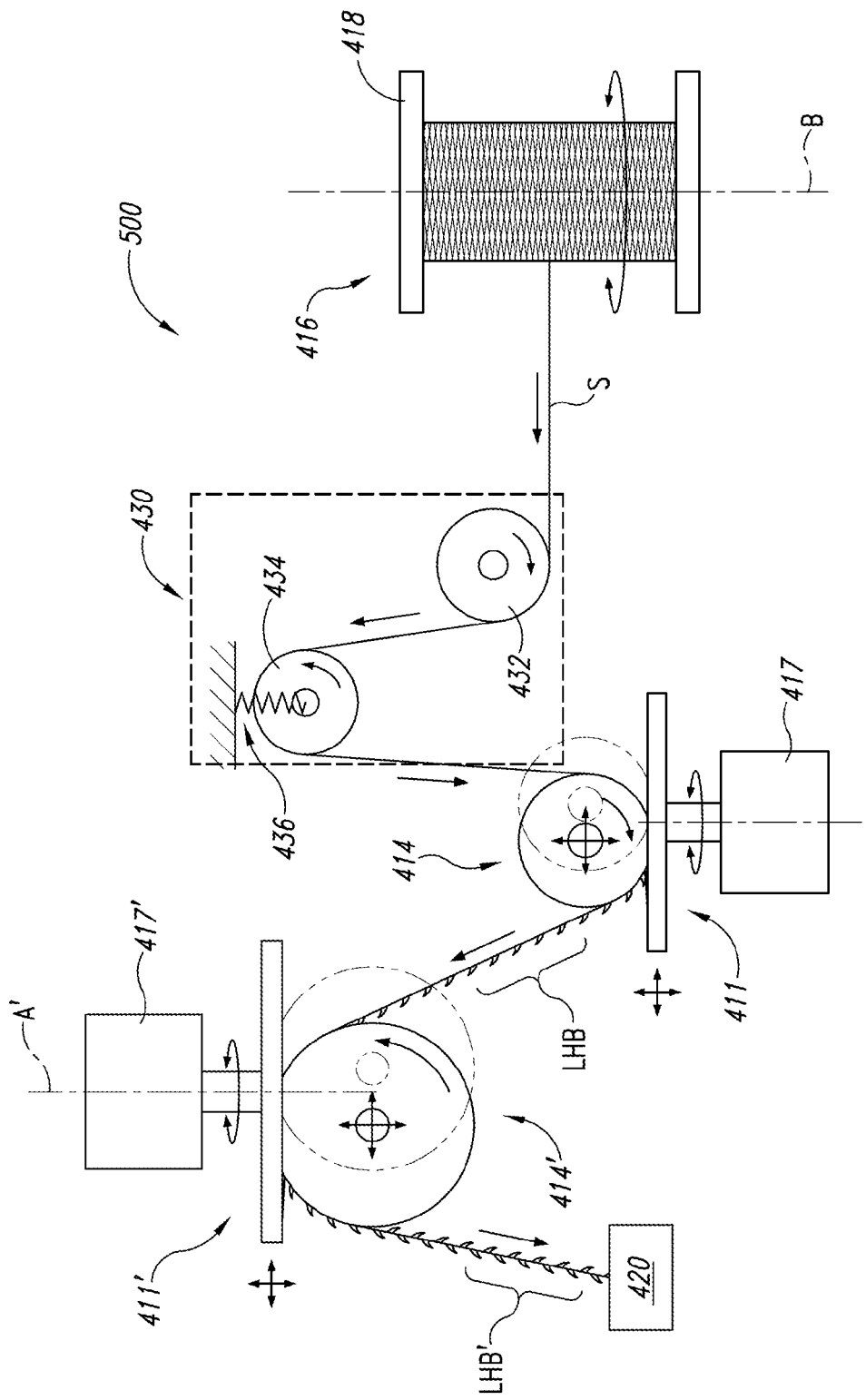
FIG. 10 is a schematic view of the apparatus for forming retainers in a continuous strand according to the embodiment shown in FIG. 9 including a strand tension maintenance mechanism.

FIG. 10 is a schematic view of an apparatus 500 for forming retainers in a continuous strand S according to another embodiment of the invention. The apparatus 500 is the same as the embodiment shown in FIG. 9 except that the apparatus 500 may additionally include a strand tension maintenance mechanism 430 positioned between the feed mechanism 416 and the first cutting and support members 411, 414 along the path of travel of the continuous strand S. As shown in FIG. 10, a plurality of intermediate sheaves or pulleys 432, 434 may be disposed at offset positions along the path of travel of the continuous strand S to regulate tension in the strand S as it travels to the first support member 414. A constant tension device 436 which may be, for example, a spring, may couple one of the intermediate sheaves, e.g., sheave 434, to a stationary frame or body to provide constant tension in the strand S. Support elements 414, 414' are also shown in a position relative to the retainer forming members 411, 411' such that left-handed retainers LHB, LHB' may be cut on the passing continuous strand S.

In each of the foregoing embodiments shown in FIGS. 1-10, a plurality of process variables are presented which, when modified singularly or in combination with other variables, can produce a strand S having theoretically countless retainer configurations thereon. These process variables include, for example, the rotational speed of the retainer forming member; the linear speed of the strand S through the apparatus; the rate or amount of twist/rotation of the strand S about its own axis; the horizontal and vertical position of the support member relative to the retainer forming member which may determine the cut depth of the formed retainer, angle of the retainer cut, and the forming of left-hand versus right-hand retainers. The foregoing variables may be selected alone or in combination depending on the gauge and composition of the strand S and/or the intended use of the sutures being produced and desired retainer configuration. Other variables may include, for example, the upwards tilt of the blade, the curvature of the cutting edge, the way the cutting edge is ground (one or both sides), the material of the blade (e.g., steel, carbide, ceramic, diamond), the coating of the blade (e.g., ceramic, diamond), and the lubrication applied during the cutting process (e.g., water, soap, gel, other conventional lubricants). Depending on the material of strand S, it may be desired to cut retainers at a temperature higher or lower than room temperature, in order to change the cutting characteristics.

In another embodiment of the apparatus (not shown), the retainer forming member may have a blade with a cutting edge directed substantially outward away from the axis about which the retainer forming member rotates. The support member may be positioned adjacent to the retainer forming member and the support and/or retainer forming members may be moveable relative to one another. The blade may be unidirectionally rotated about the axis to cut retainers in a continuous strand of suture material passing over the support member.

Figure 11A:
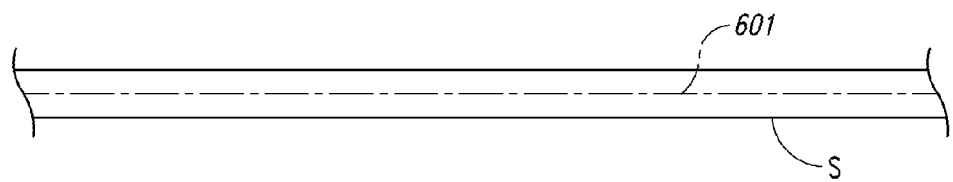
FIG. 11A is a schematic depiction of the continuous strand or suture prior to being twisted, rotated or cut.
Figure 11B:
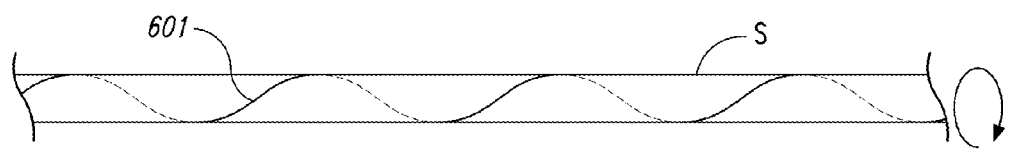
FIG. 11B is a schematic depiction of the continuous strand or suture after being twisted but prior to being cut.
Figure 11C:
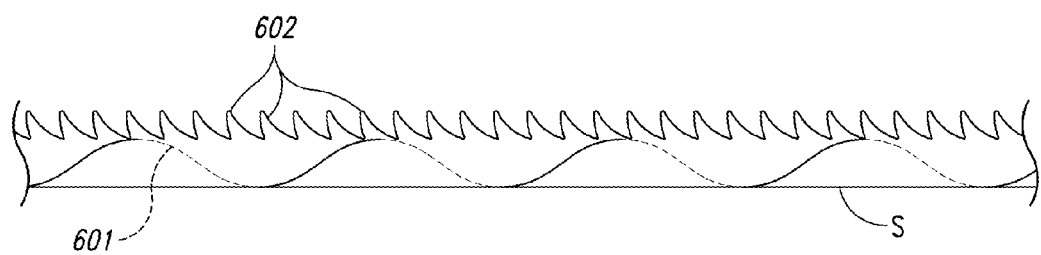
FIG. 11C is a schematic depiction of the continuous strand or suture after being twisted and cut to have retainers facing in a first direction.
Figure 11D:
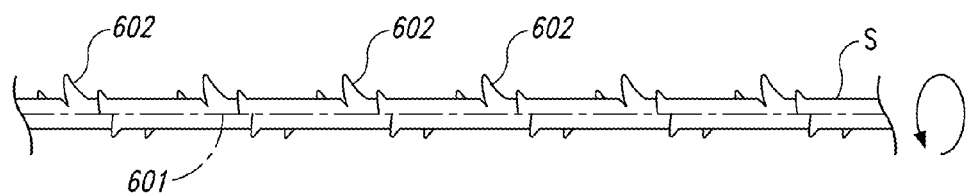
FIG. 11D is a schematic depiction of the continuous strand or suture of FIG. 11C after being untwisted from a twisted state.

FIGS. 11A-D and 12A-B are schematic depictions of the various states of the continuous strand S when twisted about its own axis, cut to form retainers, and then untwisted to reveal a plurality of retainers formed helically along the length of the strand S. FIG. 11A shows the continuous strand S prior to being twisted, rotated, or cut. In FIG. 11A the strand S is shown unmodified, with an imaginary line 601 shown to depict a line along the exterior of the strand S and extending parallel to the longitudinal axis of the strand S. FIG. 11B shows the continuous strand S during or after being twisted about its own axis but prior to being cut. Line 601 is shown extending helically about the exterior of the strand S. FIG. 11C shows the strand S after being twisted and cut to have retainers 602 facing in a first direction (i.e., left-handed retainers). FIG. 11D shows the strand S of FIG. 11C after being untwisted from a twisted state. The retainers 602 may be positioned along the length of the strand S in a helical configuration to define, for example, a one-way self-retaining suture.

Figure 12A:
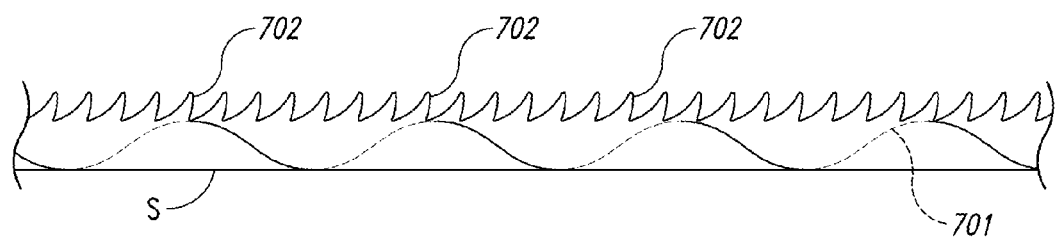
FIG. 12A is a schematic depiction of the continuous strand or suture after being twisted and cut to have retainers facing in a second direction.
Figure 12B:
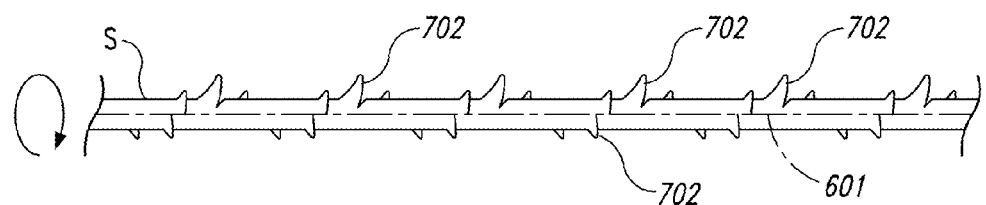
FIG. 12B is a schematic depiction of the continuous strand or suture of FIG. 12A after being untwisted from a twisted state.

FIG. 12A shows the strand S after being twisted and cut to have retainers 702 facing in a second direction (i.e., right-handed retainers). Line 601 is shown extending helically about the exterior of the twisted strand S. FIG. 12B shows the strand S of FIG. 12A after being untwisted from a twisted state. The retainers 702 may be positioned along the length of the strand S in a helical configuration to define, for example, a one-way self-retaining suture. The apparatus 10 may also be used to produce two-way self-retaining sutures (not shown).

In any of the above described embodiments, it will be appreciated that by moving the retainer forming members and support members relative to one another during operation, altering the speed of travel of the strand S, altering the twist or rotation of the strand S about its own axis, altering the rotational speed of the retainer forming member, adjusting the angle of the blade and/or the relative orientations of the cutting and support members, etc., retainers can be formed in a uniform, semi-random or complex patterns (i.e. having a combination of periods) on the exterior of the strand S.

The strand S in any of the foregoing embodiments may comprise a suture material. More particularly, the strand S may be any absorbable and/or non-absorbable material suitable to produce sutures when cut such as, for example, as described in International PCT Application Publication No. WO 2007/089864, the entirety of which is hereby incorporated by reference. Absorbable sutures are generally made of materials that will break down harmlessly in the body over time without intervention and can, therefore, be utilized internally. One exemplary natural absorbable suture material that may form the suture includes catgut (typically specially prepared beef and sheep intestine). Catgut may be untreated (plain gut), tanned with chromium salts to increase their persistence in the body (chromic gut), or heat-treated to give more rapid absorption (fast gut). The suture may also be a synthetic absorbable suture formed from synthetic polymer fibers, which may be braided or monofilament, including, for example, various blends of polyglycolic acid (PGA), lactic acid, polydioxanone (PDS), or caprolactone.

Alternatively, the suture may be a non-absorbable suture made of materials which are not metabolized by the body and must be manually removed. Non-absorbable sutures are generally used either on skin wound closure, where the sutures can be readily removed after a few weeks, or in some internal tissues in which absorbable sutures are not adequate. The suture may be formed from a natural non-absorbable suture material such as, for example, silk, which may undergo a special manufacturing process to make it adequate for use in surgery. Other suitable nonabsorbable materials for the suture may include artificial fibers such as, for example, polypropylene, polyester or nylon, or blends thereof. These materials may or may not have coatings to enhance their performance characteristics. Finally, the suture may be formed of stainless steel wire for use in, for example, orthopedic surgery or for sternal closure in cardiac surgery. Other materials may include, for example, but not limited to, polyethylene, polycarbonate, polyimide, polyamide, polyglactin, polyepsiloncaprolactone, polyortho ester, polyethyler, and/or blends thereof, and/or copolymers.

While various exemplary embodiments of the present invention have been described above, it should be understood that they have been presented by way of example only, and not limitation. Thus, the breadth and scope of the present invention should not be limited by any of the above-described exemplary embodiments, but should instead be defined only in accordance with the following claims and their equivalents.

The invention claimed is:

1. An apparatus for forming retainers on a continuous strand, comprising:
   a retainer forming member configured to rotate about a first axis and comprising a cutter, the cutter comprising a cutting edge, wherein the cutting edge of the cutter is directed substantially inward toward the first axis to define a retainer forming zone when the retainer forming member rotates about the first axis; and
   a support member arranged adjacent to the retainer forming member and configured to receive and support the continuous strand in the retainer forming zone, wherein when the retainer forming member rotates about the first axis the strand is intermittently or continuously cut by the cutting edge of the cutter.

2. The apparatus of claim 1, wherein said support member has a support member axis, wherein said support member axis is substantially perpendicular to said first axis.

3. The apparatus of claim 1, wherein when the retainer forming member rotates about the first axis the strand is cut to form a plurality of retainers.

4. A method for forming retainers on a continuous strand with an apparatus, the apparatus comprising a retainer forming member configured to rotate about a first axis and comprising a cutter, wherein a cutting edge of the cutter is directed substantially inward toward the first axis to define a retainer forming zone when the retainer forming member rotates about the first axis, and a support member arranged adjacent to the retainer forming member and configured to receive and support the continuous strand in the retainer forming zone, the method comprising:

rotating the retainer forming member of the apparatus about the first axis;

moving the continuous strand on the support member within the retainer forming zone; and intermittently or continuously cutting the strand with the cutting edge of the cutter as the retainer forming member rotates to form retainers on the strand.

5. The method of claim 4, wherein said support member has a support member axis, wherein said support member axis is substantially perpendicular to said first axis.

\* \* \* \* \*